(12) United States Patent
Hundorf et al.

(10) Patent No.: US 9,072,634 B2
(45) Date of Patent: Jul. 7, 2015

(54) DISPOSABLE ABSORBENT ARTICLE WITH SUBSTANTIALLY CONTINUOUSLY DISTRIBUTED ABSORBENT PARTICULATE POLYMER MATERIAL AND METHOD

(75) Inventors: Harald Hermann Hundorf, Bonn (DE); Holger Beruda, Schwalbach (DE); Horst Blessing, Cincinnati, OH (US); Peter Dziezok, Hochheim (DE); Axel Krause, Erftstadt (DE); Mattias Schmidt, Idstein (DE); Lutz Stelzig, Frankfurt am Main (DE)

(73) Assignee: The Procter & Gamble Company, Cincinnati, OH (US)

( * ) Notice: Subject to any disclaimer, the term of this patent is extended or adjusted under 35 U.S.C. 154(b) by 583 days.

(21) Appl. No.: 12/141,122

(22) Filed: Jun. 18, 2008

(65) Prior Publication Data

US 2008/0312617 A1    Dec. 18, 2008

Related U.S. Application Data

(60) Provisional application No. 60/936,102, filed on Jun. 18, 2007.

(51) Int. Cl.
| | |
|---|---|
| *A61F 13/15* | (2006.01) |
| *A61F 13/535* | (2006.01) |
| *A61F 13/532* | (2006.01) |
| *A61F 13/536* | (2006.01) |
| *B32B 37/14* | (2006.01) |

(Continued)

(52) U.S. Cl.
CPC ....... *A61F 13/535* (2013.01); *Y10T 428/24851* (2015.01); *Y10T 156/10* (2015.01); *A61F 13/15658* (2013.01); *A61F 13/15699* (2013.01); *A61F 13/5323* (2013.01); *A61F 13/536* (2013.01); *A61F 2013/530547* (2013.01); *B32B 37/144* (2013.01); *B32B 2309/02* (2013.01); *B32B 2309/08* (2013.01); *B32B 2310/024* (2013.01); *B32B 2555/02* (2013.01); *A61F 13/539* (2013.01); *A61F 2013/530562* (2013.01); *A61F 2013/5395* (2013.01)

(58) Field of Classification Search
USPC .......... 604/358, 364, 366–368, 370, 375, 378
See application file for complete search history.

(56) References Cited

U.S. PATENT DOCUMENTS

| | | |
|---|---|---|
| 1,733,997 A | 10/1929 | Marr |
| 1,734,499 A | 11/1929 | Marinsky |

(Continued)

FOREIGN PATENT DOCUMENTS

| | | |
|---|---|---|
| CA | 2001370 | 4/1990 |
| CA | 2291997 | 6/2000 |

(Continued)

OTHER PUBLICATIONS

International Search Report, mailed Nov. 11, 2008, PCT/IB2008/052346.

*Primary Examiner* — Michele M Kidwell
(74) *Attorney, Agent, or Firm* — Laura L. Whitmer

(57) ABSTRACT

A disposable absorbent core comprises first and second absorbent layers each comprising an absorbent particulate polymer material such that the absorbent particulate polymer material is substantially continuously distributed across an absorbent particulate polymer material area. A disposable absorbent article and method for making the absorbent core are also disclosed.

13 Claims, 12 Drawing Sheets

(51) Int. Cl.
*A61F 13/539* (2006.01)
*A61F 13/53* (2006.01)

(56) References Cited

U.S. PATENT DOCUMENTS

| | | | |
|---|---|---|---|
| 1,989,283 A | 1/1935 | Limacher | |
| 2,058,509 A | 10/1936 | Rose | |
| 2,271,676 A | 2/1942 | Bjornbak | |
| 2,450,789 A | 10/1948 | Frieman | |
| 2,508,811 A | 5/1950 | Best et al. | |
| 2,568,910 A | 9/1951 | Condylis | |
| 2,570,796 A | 10/1951 | Gross | |
| 2,570,963 A | 10/1951 | Mesmer | |
| 2,583,553 A | 1/1952 | Faure | |
| 2,705,957 A | 4/1955 | Mauro | |
| 2,788,003 A | 4/1957 | Morin | |
| 2,788,786 A | 4/1957 | Dexter | |
| 2,798,489 A | 7/1957 | Behrman | |
| 2,807,263 A | 9/1957 | Newton | |
| 2,830,589 A | 4/1958 | Doner | |
| 2,890,700 A | 6/1959 | Lönberg-Holm | |
| 2,890,701 A | 6/1959 | Weinman | |
| 2,898,912 A | 8/1959 | Adams | |
| 2,931,361 A | 4/1960 | Sostsrin | |
| 2,977,957 A | 4/1961 | Clyne | |
| 3,071,138 A * | 1/1963 | Garcia | 604/397 |
| 3,180,335 A | 4/1965 | Duncan et al. | |
| 3,207,158 A | 9/1965 | Yoshitake et al. | |
| 3,386,442 A | 6/1968 | Sabee | |
| 3,561,446 A | 2/1971 | Jones | |
| 3,572,342 A | 3/1971 | Lindquist et al. | |
| 3,572,432 A | 3/1971 | Burton | |
| 3,575,174 A | 4/1971 | Mogor | |
| 3,578,155 A | 5/1971 | Small et al. | |
| 3,606,887 A | 9/1971 | Roeder | |
| 3,610,244 A | 10/1971 | Jones | |
| 3,618,608 A | 11/1971 | Brink | |
| 3,642,001 A | 2/1972 | Sabee | |
| 3,653,381 A | 4/1972 | Warnken | |
| 3,670,731 A | 6/1972 | Harmon | |
| 3,688,767 A | 9/1972 | Goldstein | |
| 3,710,797 A | 1/1973 | Marsan | |
| 3,731,688 A | 5/1973 | Litt et al. | |
| 3,756,878 A | 9/1973 | Willot | |
| 3,774,241 A | 11/1973 | Zerkle | |
| 3,776,233 A | 12/1973 | Schaar | |
| 3,814,100 A | 6/1974 | Nystrand et al. | |
| 3,840,418 A | 10/1974 | Sabee | |
| 3,847,702 A | 11/1974 | Jones | |
| 3,848,594 A | 11/1974 | Buell | |
| 3,848,595 A | 11/1974 | Endres | |
| 3,848,597 A | 11/1974 | Endres | |
| 3,860,003 A | 1/1975 | Buell | |
| 3,863,637 A | 2/1975 | MacDonald et al. | |
| 3,882,870 A | 5/1975 | Hathaway | |
| 3,884,234 A | 5/1975 | Taylor | |
| 3,900,032 A | 8/1975 | Heurlen | |
| 3,911,173 A | 10/1975 | Sprague, Jr. | |
| 3,920,017 A | 11/1975 | Karami | |
| 3,924,626 A | 12/1975 | Lee et al. | |
| 3,926,189 A | 12/1975 | Taylor | |
| 3,929,134 A | 12/1975 | Karami | |
| 3,929,135 A | 12/1975 | Thompson | |
| 3,930,501 A | 1/1976 | Schaar | |
| 3,938,523 A | 2/1976 | Gilliland et al. | |
| 3,968,799 A | 7/1976 | Schrading | |
| 3,978,861 A | 9/1976 | Schaar | |
| 3,981,306 A | 9/1976 | Krusko | |
| 3,987,794 A | 10/1976 | Schaar | |
| 3,995,637 A | 12/1976 | Schaar | |
| 3,995,640 A | 12/1976 | Schaar | |
| 3,999,547 A | 12/1976 | Hernandez | |
| 4,014,338 A | 3/1977 | Schaar | |
| 4,034,760 A | 7/1977 | Amirsakis | |
| 4,055,180 A | 10/1977 | Karami | |
| 4,074,508 A | 2/1978 | Reid | |
| 4,084,592 A | 4/1978 | Tritsch | |
| 4,100,922 A | 7/1978 | Hernandez | |
| 4,232,674 A | 11/1980 | Melican | |
| 4,257,418 A | 3/1981 | Hessner | |
| 4,259,220 A | 3/1981 | Bunnelle et al. | |
| 4,296,750 A | 10/1981 | Woon et al. | |
| 4,315,508 A | 2/1982 | Bolick | |
| 4,324,246 A | 4/1982 | Mullane et al. | |
| 4,340,706 A | 7/1982 | Obayashi et al. | |
| 4,341,216 A | 7/1982 | Obenour | |
| 4,342,314 A | 8/1982 | Radel et al. | |
| 4,381,783 A | 5/1983 | Elias | |
| 4,388,075 A | 6/1983 | Mesek et al. | |
| 4,461,621 A | 7/1984 | Karami et al. | |
| 4,463,045 A | 7/1984 | Ahr et al. | |
| 4,469,710 A | 9/1984 | Bielley et al. | |
| 4,475,912 A | 10/1984 | Coates | |
| 4,490,148 A | 12/1984 | Beckeström | |
| 4,507,438 A | 3/1985 | Obayashi et al. | |
| 4,515,595 A | 5/1985 | Kievit | |
| 4,527,990 A | 7/1985 | Sigl | |
| 4,541,871 A | 9/1985 | Obayashi et al. | |
| 4,573,986 A | 3/1986 | Minetola et al. | |
| 4,578,072 A | 3/1986 | Lancaster | |
| 4,578,702 A | 3/1986 | Campbell | |
| 4,585,448 A | 4/1986 | Enloe | |
| 4,585,450 A | 4/1986 | Rosch et al. | |
| 4,589,878 A | 5/1986 | Mitrani | |
| 4,596,568 A | 6/1986 | Flug | |
| 4,601,717 A | 7/1986 | Blevins | |
| 4,606,964 A | 8/1986 | Wideman | |
| 4,609,518 A | 9/1986 | Curro et al. | |
| 4,610,678 A | 9/1986 | Weisman et al. | |
| 4,623,342 A | 11/1986 | Ito et al. | |
| 4,624,666 A | 11/1986 | Derossett Edmund Z | |
| 4,629,643 A | 12/1986 | Curro et al. | |
| 4,636,207 A | 1/1987 | Buell | |
| 4,641,381 A | 2/1987 | Heran et al. | |
| 4,662,875 A | 5/1987 | Hirotsu et al. | |
| 4,666,983 A | 5/1987 | Tsubakimoto et al. | |
| 4,670,011 A | 6/1987 | Mesek | |
| 4,670,012 A | 6/1987 | Johnson | |
| 4,680,030 A | 7/1987 | Coates et al. | |
| 4,681,579 A | 7/1987 | Toussant et al. | |
| 4,681,581 A | 7/1987 | Coates | |
| 4,681,793 A | 7/1987 | Linman et al. | |
| 4,690,680 A | 9/1987 | Higgins | |
| 4,695,278 A | 9/1987 | Lawson | |
| 4,699,622 A | 10/1987 | Toussant et al. | |
| 4,704,115 A | 11/1987 | Buell | |
| 4,704,116 A | 11/1987 | Enloe | |
| 4,710,189 A | 12/1987 | Lash | |
| 4,731,066 A | 3/1988 | Korpman | |
| 4,731,070 A | 3/1988 | Koci | |
| RE32,649 E | 4/1988 | Brandt et al. | |
| 4,747,846 A | 5/1988 | Boland et al. | |
| 4,773,905 A | 9/1988 | Molee | |
| 4,784,892 A | 11/1988 | Storey et al. | |
| 4,785,996 A | 11/1988 | Ziecker et al. | |
| 4,787,896 A | 11/1988 | Houghton et al. | |
| 4,795,454 A | 1/1989 | Dragoo | |
| 4,802,884 A | 2/1989 | Fröidh et al. | |
| 4,808,176 A | 2/1989 | Kielpikowski | |
| 4,808,178 A | 2/1989 | Aziz | |
| 4,834,735 A * | 5/1989 | Alemany et al. | 604/368 |
| 4,834,740 A | 5/1989 | Suzuki et al. | |
| 4,834,742 A | 5/1989 | Wilson et al. | |
| 4,838,886 A | 6/1989 | Kent | |
| 4,842,666 A | 6/1989 | Werenicz | |
| 4,846,815 A | 7/1989 | Scripps | |
| 4,846,825 A | 7/1989 | Enloe et al. | |
| 4,848,815 A | 7/1989 | Molloy | |
| 4,861,652 A | 8/1989 | Lippert et al. | |
| 4,869,724 A | 9/1989 | Scripps | |
| 4,886,697 A | 12/1989 | Perdelwitz, Jr et al. | |
| 4,888,231 A | 12/1989 | Angstadt | |
| 4,892,528 A | 1/1990 | Suzuki et al. | |
| 4,892,535 A | 1/1990 | Bjornberg | |

(56) References Cited

U.S. PATENT DOCUMENTS

| | | |
|---|---|---|
| 4,892,536 A | 1/1990 | DesMarais et al. |
| 4,894,060 A | 1/1990 | Nestegard |
| 4,894,277 A | 1/1990 | Akasaki |
| 4,900,317 A | 2/1990 | Buell |
| 4,904,251 A | 2/1990 | Igaue et al. |
| 4,909,802 A | 3/1990 | Ahr et al. |
| 4,909,803 A | 3/1990 | Aziz et al. |
| 4,936,839 A | 6/1990 | Molee |
| 4,940,463 A | 7/1990 | Leathers et al. |
| 4,940,464 A | 7/1990 | Van Gompel et al. |
| 4,946,527 A | 8/1990 | Battrell |
| 4,950,264 A | 8/1990 | Osborn |
| 4,960,477 A | 10/1990 | Mesek |
| 4,963,140 A | 10/1990 | Robertson et al. |
| 4,968,313 A | 11/1990 | Sabee |
| 4,990,147 A | 2/1991 | Freeland |
| 4,994,053 A | 2/1991 | Lang |
| 5,006,394 A | 4/1991 | Baird |
| 5,019,063 A | 5/1991 | Marsan et al. |
| 5,019,072 A | 5/1991 | Polski |
| 5,021,051 A | 6/1991 | Hiuke |
| 5,030,314 A | 7/1991 | Lang |
| 5,032,120 A | 7/1991 | Freeland et al. |
| 5,034,008 A | 7/1991 | Breitkopf |
| 5,037,416 A | 8/1991 | Allen et al. |
| 5,071,414 A | 12/1991 | Elliott |
| 5,072,687 A | 12/1991 | Mitchell |
| 5,085,654 A | 2/1992 | Buell |
| 5,087,255 A | 2/1992 | Sims et al. |
| 5,092,861 A | 3/1992 | Nomura et al. |
| 5,102,597 A | 4/1992 | Roe et al. |
| 5,114,420 A | 5/1992 | Igaue et al. |
| 5,124,188 A | 6/1992 | Roe et al. |
| 5,135,522 A | 8/1992 | Fahrenkrug et al. |
| 5,137,537 A | 8/1992 | Herron et al. |
| D329,697 S | 9/1992 | Fahrenkrug et al. |
| 5,143,679 A | 9/1992 | Weber et al. |
| 5,147,343 A | 9/1992 | Kellenberger |
| 5,147,345 A | 9/1992 | Young et al. |
| 5,149,334 A | 9/1992 | Lahrman et al. |
| 5,149,335 A | 9/1992 | Kellenberger et al. |
| 5,151,091 A | 9/1992 | Glaug |
| 5,151,092 A | 9/1992 | Buell et al. |
| 5,156,793 A | 10/1992 | Buell et al. |
| 5,167,653 A | 12/1992 | Igaue et al. |
| 5,167,897 A | 12/1992 | Weber et al. |
| 5,175,046 A | 12/1992 | Nguyen |
| 5,180,622 A | 1/1993 | Berg et al. |
| 5,190,563 A | 3/1993 | Herron et al. |
| 5,190,606 A | 3/1993 | Merkatoris et al. |
| 5,204,997 A | 4/1993 | Suzuki et al. |
| 5,221,274 A | 6/1993 | Buell et al. |
| 5,235,515 A | 8/1993 | Ungpiyakul et al. |
| 5,242,436 A | 9/1993 | Weil et al. |
| 5,246,431 A | 9/1993 | Minetola et al. |
| 5,246,432 A | 9/1993 | Suzuki et al. |
| 5,246,433 A | 9/1993 | Hasse et al. |
| 5,248,309 A | 9/1993 | Serbiak et al. |
| 5,260,345 A | 11/1993 | DesMarais et al. |
| 5,269,775 A | 12/1993 | Freeland et al. |
| 5,281,683 A | 1/1994 | Yano et al. |
| H1298 H | 4/1994 | Ahr |
| 5,300,565 A | 4/1994 | Berg et al. |
| 5,312,386 A | 5/1994 | Correa et al. |
| 5,331,059 A | 7/1994 | Engelhardt et al. |
| 5,336,552 A | 8/1994 | Strack et al. |
| 5,348,547 A | 9/1994 | Payne et al. |
| 5,358,500 A | 10/1994 | La Von et al. |
| 5,366,782 A | 11/1994 | Curro et al. |
| 5,387,207 A | 2/1995 | Dyer et al. |
| 5,387,209 A | 2/1995 | Yamamoto et al. |
| 5,389,095 A | 2/1995 | Suzuki |
| 5,397,316 A | 3/1995 | LaVon et al. |
| 5,399,175 A | 3/1995 | Glaug |
| 5,401,792 A | 3/1995 | Babu et al. |
| 5,409,771 A | 4/1995 | Dahmen et al. |
| H1440 H | 5/1995 | New et al. |
| 5,411,497 A | 5/1995 | Tanzer et al. |
| 5,415,644 A | 5/1995 | Enloe |
| 5,425,725 A | 6/1995 | Tanzer et al. |
| 5,433,715 A | 7/1995 | Tanzer et al. |
| 5,451,219 A | 9/1995 | Suzuki |
| 5,451,442 A | 9/1995 | Pieniak |
| 5,460,622 A | 10/1995 | Dragoo et al. |
| 5,462,541 A | 10/1995 | Bruemmer et al. |
| 5,476,458 A | 12/1995 | Glaug et al. |
| 5,486,166 A | 1/1996 | Bishop et al. |
| 5,490,846 A | 2/1996 | Ellis et al. |
| 5,492,962 A | 2/1996 | Lahrman et al. |
| 5,494,622 A | 2/1996 | Heath et al. |
| 5,499,978 A | 3/1996 | Buell et al. |
| 5,507,736 A | 4/1996 | Clear et al. |
| 5,507,895 A | 4/1996 | Suekane |
| 5,509,915 A | 4/1996 | Hanson et al. |
| 5,514,104 A | 5/1996 | Cole |
| 5,518,801 A | 5/1996 | Chappell et al. |
| 5,520,674 A | 5/1996 | Lavon et al. |
| 5,522,810 A | 6/1996 | Allen, Jr. |
| 5,527,300 A | 6/1996 | Sauer |
| 5,531,730 A | 7/1996 | Dreier |
| 5,532,323 A | 7/1996 | Yano et al. |
| 5,542,943 A | 8/1996 | Sageser |
| 5,549,592 A | 8/1996 | Fries et al. |
| 5,549,593 A | 8/1996 | Ygge et al. |
| 5,549,791 A | 8/1996 | Herron et al. |
| 5,554,145 A | 9/1996 | Roe et al. |
| 5,560,878 A | 10/1996 | Dragoo et al. |
| 5,562,634 A | 10/1996 | Flumene et al. |
| 5,562,646 A | 10/1996 | Goldman et al. |
| 5,569,234 A | 10/1996 | Buell et al. |
| 5,571,096 A | 11/1996 | Dobrin et al. |
| 5,574,121 A | 11/1996 | Irie et al. |
| 5,580,411 A | 12/1996 | Nease et al. |
| 5,584,829 A | 12/1996 | Lavash et al. |
| 5,591,152 A | 1/1997 | Buell et al. |
| 5,591,155 A | 1/1997 | Nishikawa et al. |
| 5,593,399 A | 1/1997 | Tanzer et al. |
| 5,599,335 A | 2/1997 | Goldman et al. |
| 5,601,542 A | 2/1997 | Melius et al. |
| 5,607,414 A | 3/1997 | Richards et al. |
| 5,607,416 A | 3/1997 | Yamamoto et al. |
| 5,607,537 A | 3/1997 | Johnson et al. |
| 5,607,760 A | 3/1997 | Roe |
| 5,609,587 A | 3/1997 | Roe |
| 5,609,588 A * | 3/1997 | DiPalma et al. .............. 604/369 |
| 5,611,879 A | 3/1997 | Morman |
| 5,613,959 A | 3/1997 | Roessler et al. |
| 5,613,960 A | 3/1997 | Mizutani |
| 5,614,283 A | 3/1997 | Potnis et al. |
| 5,622,589 A | 4/1997 | Johnson et al. |
| 5,624,423 A | 4/1997 | Anjur |
| 5,624,424 A | 4/1997 | Saisaka et al. |
| 5,625,222 A | 4/1997 | Yoneda et al. |
| 5,626,571 A | 5/1997 | Young et al. |
| 5,628,741 A | 5/1997 | Buell et al. |
| 5,635,191 A | 6/1997 | Roe et al. |
| 5,635,271 A | 6/1997 | Zafiroglu |
| 5,637,106 A | 6/1997 | Mitchell Deceased Winalee G |
| 5,643,238 A | 7/1997 | Baker |
| 5,643,243 A | 7/1997 | Klemp |
| 5,643,588 A | 7/1997 | Roe et al. |
| 5,649,914 A | 7/1997 | Glaug |
| 5,650,214 A | 7/1997 | Anderson |
| H1674 H | 8/1997 | Ames et al. |
| 5,658,268 A | 8/1997 | Johns et al. |
| 5,662,634 A | 9/1997 | Yamamoto et al. |
| 5,662,638 A | 9/1997 | Johnson et al. |
| 5,674,215 A | 10/1997 | Ronnberg |
| 5,683,374 A | 11/1997 | Yamamoto |
| 5,685,874 A | 11/1997 | Buell et al. |
| 5,690,627 A | 11/1997 | Clear et al. |
| 5,691,035 A | 11/1997 | Chappell et al. |
| 5,695,488 A | 12/1997 | Sosalla |
| 5,700,254 A | 12/1997 | McDowall et al. |

(56) References Cited

U.S. PATENT DOCUMENTS

| | | |
|---|---|---|
| 5,702,376 A | 12/1997 | Glaug |
| 5,714,156 A | 2/1998 | Schmidt et al. |
| 5,723,087 A | 3/1998 | Chappell et al. |
| 5,733,275 A | 3/1998 | Davis et al. |
| 5,749,866 A | 5/1998 | Roe et al. |
| 5,752,947 A | 5/1998 | Awolin |
| 5,756,039 A | 5/1998 | McFall et al. |
| H1732 H | 6/1998 | Johnson |
| 5,762,641 A | 6/1998 | Bewick-Sonntag et al. |
| 5,766,388 A | 6/1998 | Pelley |
| 5,766,389 A | 6/1998 | Brandon et al. |
| 5,772,825 A | 6/1998 | Schmitz |
| 5,776,121 A | 7/1998 | Roe et al. |
| 5,779,831 A | 7/1998 | Schmitz |
| 5,788,684 A | 8/1998 | Abuto et al. |
| 5,795,345 A | 8/1998 | Mizutani |
| 5,797,892 A | 8/1998 | Glaug |
| 5,797,894 A | 8/1998 | Cadieux et al. |
| 5,807,365 A | 9/1998 | Luceri |
| 5,810,796 A | 9/1998 | Kimura et al. |
| 5,810,800 A | 9/1998 | Hunter et al. |
| 5,814,035 A | 9/1998 | Gryskiewicz et al. |
| 5,820,618 A | 10/1998 | Roberts et al. |
| 5,827,257 A | 10/1998 | Fujioka |
| 5,830,202 A | 11/1998 | Bogdanski et al. |
| 5,833,678 A | 11/1998 | Ashton et al. |
| 5,837,789 A | 11/1998 | Stockhausen et al. |
| 5,843,059 A | 12/1998 | Niemeyer et al. |
| 5,846,231 A | 12/1998 | Fujioka et al. |
| 5,846,232 A | 12/1998 | Serbiak et al. |
| 5,849,816 A | 12/1998 | Suskind et al. |
| 5,851,204 A | 12/1998 | Mizutani |
| 5,855,572 A | 1/1999 | Schmidt |
| 5,858,013 A | 1/1999 | Kling |
| 5,865,823 A | 2/1999 | Curro |
| 5,865,824 A | 2/1999 | Chen |
| 5,873,868 A | 2/1999 | Nakahata |
| 5,876,391 A | 3/1999 | Roe et al. |
| 5,891,118 A | 4/1999 | Toyoshima |
| 5,891,544 A | 4/1999 | Chappell et al. |
| 5,897,545 A | 4/1999 | Kline et al. |
| 5,904,673 A | 5/1999 | Roe et al. |
| 5,928,184 A | 7/1999 | Etheredge |
| 5,931,825 A | 8/1999 | Kuen et al. |
| 5,938,648 A | 8/1999 | Lavon et al. |
| 5,938,650 A | 8/1999 | Baer et al. |
| 5,941,862 A | 8/1999 | Haynes et al. |
| 5,944,706 A | 8/1999 | Palumbo et al. |
| 5,947,949 A | 9/1999 | Inoue et al. |
| 5,951,536 A | 9/1999 | Osborn, III et al. |
| 5,957,908 A | 9/1999 | Kline et al. |
| 5,968,025 A | 10/1999 | Roe et al. |
| 5,968,029 A | 10/1999 | Chappell et al. |
| 5,980,500 A | 11/1999 | Shimizu et al. |
| 5,981,824 A | 11/1999 | Luceri |
| 5,989,236 A | 11/1999 | Roe et al. |
| 6,004,306 A | 12/1999 | Robles et al. |
| 6,022,430 A | 2/2000 | Blenke et al. |
| 6,022,431 A | 2/2000 | Blenke et al. |
| 6,042,673 A | 3/2000 | Johnson et al. |
| 6,050,984 A | 4/2000 | Fujioka |
| 6,054,631 A | 4/2000 | Gent |
| 6,060,115 A | 5/2000 | Borowski et al. |
| 6,068,620 A | 5/2000 | Chmielewski |
| 6,080,909 A | 6/2000 | Osterdahl et al. |
| 6,083,210 A | 7/2000 | Young et al. |
| 6,090,994 A | 7/2000 | Chen |
| 6,091,336 A | 7/2000 | Zand |
| 6,099,515 A | 8/2000 | Sugito |
| 6,102,892 A | 8/2000 | Putzer et al. |
| 6,103,814 A | 8/2000 | van Drongelen et al. |
| 6,107,537 A | 8/2000 | Elder et al. |
| 6,110,157 A | 8/2000 | Schmidt |
| 6,117,121 A | 9/2000 | Faulks et al. |
| 6,117,803 A | 9/2000 | Morman et al. |
| 6,120,486 A | 9/2000 | Toyoda et al. |
| 6,120,487 A | 9/2000 | Ashton |
| 6,120,489 A | 9/2000 | Johnson et al. |
| 6,120,866 A | 9/2000 | Arakawa et al. |
| 6,121,509 A | 9/2000 | Ashraf et al. |
| 6,129,717 A | 10/2000 | Fujioka et al. |
| 6,129,720 A | 10/2000 | Blenke et al. |
| 6,132,411 A | 10/2000 | Huber et al. |
| 6,139,912 A | 10/2000 | Onuschak |
| 6,143,821 A | 11/2000 | Houben |
| 6,152,908 A | 11/2000 | Widlund |
| 6,156,023 A | 12/2000 | Yoshioka |
| 6,156,424 A | 12/2000 | Taylor |
| 6,160,197 A | 12/2000 | Lassen |
| 6,165,160 A | 12/2000 | Suzuki et al. |
| 6,174,302 B1 | 1/2001 | Kumasaka |
| 6,177,606 B1 | 1/2001 | Etheredge |
| 6,177,607 B1 | 1/2001 | Blaney et al. |
| 6,186,996 B1 | 2/2001 | Martin |
| 6,210,386 B1 | 4/2001 | Inoue |
| 6,210,390 B1 | 4/2001 | Karlsson |
| 6,231,556 B1 | 5/2001 | Osborn, III |
| 6,231,566 B1 | 5/2001 | Lai |
| 6,238,380 B1 | 5/2001 | Sasaki |
| 6,241,716 B1 | 6/2001 | Rönnberg |
| 6,254,294 B1 | 7/2001 | Muhar |
| 6,258,996 B1 | 7/2001 | Goldman |
| 6,265,488 B1 | 7/2001 | Fujino et al. |
| 6,306,122 B1 | 10/2001 | Narawa et al. |
| 6,315,765 B1 | 11/2001 | Datta |
| 6,322,552 B1 | 11/2001 | Blenke et al. |
| 6,325,787 B1 | 12/2001 | Roe et al. |
| 6,326,525 B1 | 12/2001 | Hamajima |
| 6,334,858 B1 | 1/2002 | Rönnberg et al. |
| 6,336,922 B1 | 1/2002 | Van Gompel et al. |
| 6,340,611 B1 | 1/2002 | Shimizu |
| 6,342,715 B1 | 1/2002 | Shimizu |
| 6,350,332 B1 | 2/2002 | Thomas et al. |
| 6,368,687 B1 | 4/2002 | Joseph et al. |
| 6,371,948 B1 | 4/2002 | Mizutani |
| 6,372,952 B1 | 4/2002 | Lash et al. |
| 6,375,644 B2 | 4/2002 | Mizutani |
| 6,376,034 B1 | 4/2002 | Brander |
| 6,383,431 B1 | 5/2002 | Dobrin et al. |
| 6,383,960 B1 | 5/2002 | Everett et al. |
| 6,394,989 B2 | 5/2002 | Mizutani |
| 6,402,729 B1 | 6/2002 | Boberg et al. |
| 6,402,731 B1 | 6/2002 | Suprise et al. |
| 6,403,857 B1 | 6/2002 | Gross et al. |
| 6,409,883 B1 | 6/2002 | Makolin |
| 6,410,820 B1 | 6/2002 | McFall et al. |
| 6,410,822 B1 | 6/2002 | Mizutani |
| 6,413,248 B1 | 7/2002 | Mizutani |
| 6,413,249 B1 | 7/2002 | Turi et al. |
| 6,414,214 B1 | 7/2002 | Engelhardt et al. |
| 6,419,667 B1 | 7/2002 | Avalon et al. |
| 6,423,046 B1 | 7/2002 | Fujioka et al. |
| 6,423,048 B1 | 7/2002 | Suzuki et al. |
| 6,423,884 B1 | 7/2002 | Oehmen |
| 6,429,350 B1 | 8/2002 | Tanzer et al. |
| 6,432,094 B1 | 8/2002 | Fujioka et al. |
| 6,432,098 B1 | 8/2002 | Kline et al. |
| 6,432,099 B2 | 8/2002 | Rönnberg |
| 6,437,214 B1 | 8/2002 | Everett et al. |
| 6,441,268 B1 | 8/2002 | Edwardsson |
| 6,443,933 B1 | 9/2002 | Suzuki et al. |
| 6,444,064 B1 | 9/2002 | Henry et al. |
| 6,447,496 B1 | 9/2002 | Mizutani |
| 6,458,111 B1 | 10/2002 | Onishi et al. |
| 6,458,877 B1 | 10/2002 | Ahmed et al. |
| 6,459,016 B1 * | 10/2002 | Rosenfeld et al. ............ 604/378 |
| 6,461,342 B1 | 10/2002 | Tanji et al. |
| 6,461,343 B1 | 10/2002 | Schaefer et al. |
| 6,472,478 B1 | 10/2002 | Funk et al. |
| 6,475,201 B2 | 11/2002 | Saito et al. |
| 6,494,872 B1 | 12/2002 | Suzuki et al. |
| 6,494,873 B2 | 12/2002 | Karlsson et al. |
| 6,500,159 B1 | 12/2002 | Carvalho |
| 6,503,233 B1 | 1/2003 | Chen |

(56) References Cited

U.S. PATENT DOCUMENTS

| | | |
|---|---|---|
| 6,503,979 B1 | 1/2003 | Funk et al. |
| 6,506,186 B1 | 1/2003 | Roessler |
| 6,506,961 B1 | 1/2003 | Levy |
| 6,515,195 B1 | 2/2003 | Lariviere |
| 6,517,525 B1 | 2/2003 | Berthou |
| 6,518,479 B1 | 2/2003 | Graef |
| 6,520,947 B1 | 2/2003 | Tilly et al. |
| 6,521,811 B1 | 2/2003 | Lassen |
| 6,521,812 B1 | 2/2003 | Howard |
| 6,524,294 B1 | 2/2003 | Hilston et al. |
| 6,525,240 B1 | 2/2003 | Graef |
| 6,528,698 B2 | 3/2003 | Mizutani et al. |
| 6,531,025 B1 | 3/2003 | Lender et al. |
| 6,531,027 B1 | 3/2003 | Lender et al. |
| 6,534,149 B1 | 3/2003 | Daley et al. |
| 6,559,081 B1 | 5/2003 | Erspamer et al. |
| 6,559,239 B1 | 5/2003 | Riegel et al. |
| 6,562,168 B1 | 5/2003 | Schmitt et al. |
| 6,562,192 B1 | 5/2003 | Hamilton |
| 6,569,137 B2 | 5/2003 | Suzuki et al. |
| 6,573,422 B1 | 6/2003 | Rosenfeld |
| 6,585,713 B1 | 7/2003 | LeMahieu et al. |
| 6,585,858 B1 | 7/2003 | Otto et al. |
| 6,602,234 B2 | 8/2003 | Klemp et al. |
| 6,605,070 B2 | 8/2003 | Ludwig et al. |
| 6,605,172 B1 | 8/2003 | Anderson et al. |
| 6,605,752 B2 | 8/2003 | Magnusson et al. |
| 6,610,900 B1 | 8/2003 | Tanzer |
| 6,630,054 B1 | 10/2003 | Graef |
| 6,632,209 B1 | 10/2003 | Chmielewski |
| 6,632,504 B1 | 10/2003 | Gillespie et al. |
| 6,645,569 B2 | 11/2003 | Cramer et al. |
| 6,646,180 B1 | 11/2003 | Chmielewski |
| 6,648,869 B1 | 11/2003 | Schlinz et al. |
| 6,648,870 B2 | 11/2003 | Itoh et al. |
| 6,648,871 B2 | 11/2003 | Kusibojoska et al. |
| 6,649,807 B2 | 11/2003 | Mizutani |
| 6,649,810 B1 | 11/2003 | Minato et al. |
| 6,657,015 B1 | 12/2003 | Riegel et al. |
| 6,657,102 B2 | 12/2003 | Furuya |
| 6,667,424 B1 | 12/2003 | Hamilton |
| 6,670,522 B1 | 12/2003 | Graef |
| 6,673,982 B1 | 1/2004 | Chen |
| 6,673,983 B1 | 1/2004 | Graef |
| 6,673,985 B2 | 1/2004 | Mizutani |
| 6,682,515 B1 | 1/2004 | Mizutani et al. |
| 6,682,516 B2 | 1/2004 | Johnston |
| 6,689,115 B1 | 2/2004 | Popp et al. |
| 6,689,934 B2 | 2/2004 | Dodge, II et al. |
| 6,695,827 B2 | 2/2004 | Chen |
| 6,700,034 B1 | 3/2004 | Lindsay et al. |
| 6,703,538 B2 | 3/2004 | Lassen |
| 6,705,465 B2 | 3/2004 | Ling et al. |
| 6,706,943 B2 | 3/2004 | Onishi |
| 6,710,224 B2 | 3/2004 | Chmielewski et al. |
| 6,710,225 B1 | 3/2004 | Everett et al. |
| 6,716,205 B2 | 4/2004 | Popp et al. |
| 6,716,441 B1 | 4/2004 | Osborne et al. |
| 6,717,029 B2 | 4/2004 | Baker |
| 6,726,668 B2 | 4/2004 | Underhill et al. |
| 6,726,792 B1 | 4/2004 | Johnson et al. |
| 6,734,335 B1 | 5/2004 | Graef |
| 6,790,798 B1 | 9/2004 | Suzuki et al. |
| 6,809,158 B2 | 10/2004 | Ikeuchi et al. |
| 6,818,083 B2 | 11/2004 | McAmish et al. |
| 6,830,800 B2 | 12/2004 | Curro et al. |
| 6,840,929 B2 | 1/2005 | Kurata |
| 6,846,374 B2 | 1/2005 | Popp |
| 6,858,771 B2 | 2/2005 | Yoshimasa et al. |
| 6,863,933 B2 | 3/2005 | Cramer et al. |
| 6,863,960 B2 | 3/2005 | Curro et al. |
| 6,867,345 B2 | 3/2005 | Shimoe et al. |
| 6,867,346 B1 | 3/2005 | Dopps |
| 6,878,433 B2 | 4/2005 | Curro et al. |
| 6,880,211 B2 | 4/2005 | Jackson et al. |
| 6,891,080 B2 | 5/2005 | Minato |
| 6,904,865 B2 | 6/2005 | Klofta |
| 6,911,574 B1 | 6/2005 | Mizutani |
| 6,923,797 B2 | 8/2005 | Shinohara et al. |
| 6,926,703 B2 | 8/2005 | Sugito |
| 6,929,629 B2 | 8/2005 | Drevik et al. |
| 6,939,914 B2 | 9/2005 | Qin et al. |
| 6,946,585 B2 | 9/2005 | Brown |
| 6,953,451 B2 | 10/2005 | Berba |
| 6,955,733 B2 | 10/2005 | Miller |
| 6,962,578 B1 | 11/2005 | Lavon |
| 6,962,645 B2 | 11/2005 | Graef |
| 6,965,058 B1 | 11/2005 | Raidel |
| 6,969,781 B2 | 11/2005 | Graef |
| 6,972,010 B2 | 12/2005 | Pesce et al. |
| 6,972,011 B2 | 12/2005 | Maeda et al. |
| 6,979,564 B2 | 12/2005 | Glucksmann et al. |
| 7,001,167 B2 | 2/2006 | Venturino |
| 7,014,632 B2 | 3/2006 | Takino et al. |
| 7,015,370 B2 | 3/2006 | Watanabe |
| 7,037,299 B2 | 5/2006 | Turi et al. |
| 7,037,571 B2 | 5/2006 | Fish et al. |
| 7,048,726 B2 | 5/2006 | Kusagawa et al. |
| 7,056,311 B2 | 6/2006 | Kinoshita |
| 7,067,711 B2 | 6/2006 | Kuroda et al. |
| 7,073,373 B2 | 7/2006 | La Fortune |
| 7,078,583 B2 | 7/2006 | Kudo |
| 7,090,665 B2 | 8/2006 | Ohashi |
| 7,108,759 B2 | 9/2006 | You |
| 7,108,916 B2 | 9/2006 | Ehrnsperger et al. |
| 7,112,621 B2 | 9/2006 | Rohrbaugh et al. |
| 7,122,713 B2 | 10/2006 | Komatsu |
| 7,125,470 B2 | 10/2006 | Graef |
| 7,132,585 B2 | 11/2006 | Kudo |
| 7,147,628 B2 | 12/2006 | Drevik |
| 7,150,729 B2 | 12/2006 | Shimada |
| 7,154,019 B2 | 12/2006 | Mishima et al. |
| 7,160,281 B2 | 1/2007 | Leminh et al. |
| 7,166,190 B2 | 1/2007 | Graef |
| 7,169,136 B2 | 1/2007 | Otsubo et al. |
| 7,183,360 B2 | 2/2007 | Daniel et al. |
| 7,189,888 B2 | 3/2007 | Wang et al. |
| 7,196,241 B2 | 3/2007 | Kinoshita |
| 7,199,211 B2 | 4/2007 | Popp et al. |
| 7,204,830 B2 | 4/2007 | Mishima |
| 7,207,978 B2 | 4/2007 | Takino |
| 7,219,403 B2 | 5/2007 | Miyamoto et al. |
| 7,220,251 B2 | 5/2007 | Otsubo et al. |
| 7,250,481 B2 | 7/2007 | Jaworek et al. |
| 7,252,657 B2 | 8/2007 | Mishima |
| 7,265,258 B2 | 9/2007 | Hamilton |
| 7,311,968 B2 | 12/2007 | Ehrnsperger et al. |
| 7,312,372 B2 | 12/2007 | Miyama et al. |
| 7,318,820 B2 | 1/2008 | LaVon et al. |
| 7,329,244 B2 | 2/2008 | Otsubo |
| 7,329,246 B2 | 2/2008 | Kinoshita |
| 7,335,810 B2 | 2/2008 | Yoshimasa et al. |
| 7,377,914 B2 | 5/2008 | LaVon |
| 7,429,689 B2 | 9/2008 | Chen |
| 7,435,244 B2 | 10/2008 | Schroer et al. |
| 7,465,373 B2 | 12/2008 | Graef |
| 7,500,969 B2 | 3/2009 | Mishima et al. |
| 7,504,552 B2 | 3/2009 | Tamura et al. |
| 7,521,109 B2 | 4/2009 | Suzuki et al. |
| 7,521,587 B2 | 4/2009 | Busam et al. |
| 7,537,832 B2 | 5/2009 | Carlucci et al. |
| 7,547,815 B2 | 6/2009 | Ohashi et al. |
| 7,550,646 B2 | 6/2009 | Tamura et al. |
| 7,563,257 B2 | 7/2009 | Nakajima et al. |
| 7,588,561 B2 | 9/2009 | Kenmochi et al. |
| 7,594,904 B2 | 9/2009 | Rosenfeld |
| 7,625,363 B2 | 12/2009 | Yoshimasa et al. |
| 7,641,642 B2 | 1/2010 | Murai et al. |
| 7,648,490 B2 | 1/2010 | Kuroda et al. |
| 7,652,111 B2 | 1/2010 | Hermeling et al. |
| 7,666,173 B2 | 2/2010 | Mishima et al. |
| 7,666,174 B2 | 2/2010 | Onishi et al. |
| 7,686,790 B2 | 3/2010 | Rasmussen et al. |
| 7,687,596 B2 | 3/2010 | Hermeling et al. |

(56) References Cited

U.S. PATENT DOCUMENTS

| | | |
|---|---|---|
| 7,695,461 B2 | 4/2010 | Rosenfeld |
| 7,696,402 B2 | 4/2010 | Nishikawa et al. |
| 7,708,725 B2 | 5/2010 | Tamagawa et al. |
| 7,717,150 B2 | 5/2010 | Manabe et al. |
| 7,722,587 B2 | 5/2010 | Suzuki et al. |
| 7,722,590 B2 | 5/2010 | Tsuji et al. |
| 7,727,217 B2 | 6/2010 | Hancock-Cooke |
| 7,736,351 B2 | 6/2010 | Nigam |
| 7,744,576 B2 | 6/2010 | Busam et al. |
| 7,744,578 B2 | 6/2010 | Tanio et al. |
| 7,750,203 B2 | 7/2010 | Becker et al. |
| 7,754,822 B2 | 7/2010 | Daniel et al. |
| 7,754,940 B2 | 7/2010 | Brisebois et al. |
| 7,759,540 B2 * | 7/2010 | Litvay et al. .................. 604/379 |
| 7,763,004 B2 | 7/2010 | Beck |
| 7,767,875 B2 | 8/2010 | Olson |
| 7,767,878 B2 | 8/2010 | Suzuki |
| 7,772,420 B2 | 8/2010 | Hermeling et al. |
| 7,786,341 B2 | 8/2010 | Schneider et al. |
| 7,795,492 B2 | 9/2010 | Vartiainen |
| 7,803,145 B2 | 9/2010 | Rosenfeld |
| 7,825,291 B2 | 11/2010 | Elfsberg et al. |
| 7,850,672 B2 | 12/2010 | Guidotti et al. |
| 7,851,667 B2 | 12/2010 | Becker et al. |
| 7,855,314 B2 | 12/2010 | Hanao et al. |
| 7,857,797 B2 | 12/2010 | Kudo et al. |
| 7,858,842 B2 | 12/2010 | Komatsu et al. |
| 7,884,259 B2 | 2/2011 | Hanao et al. |
| 7,888,549 B2 | 2/2011 | Jansson et al. |
| 7,910,797 B2 | 3/2011 | Nandrea |
| 7,935,207 B2 | 5/2011 | Zhao |
| 7,935,861 B2 | 5/2011 | Suzuki |
| 7,938,813 B2 | 5/2011 | Wang et al. |
| 7,942,858 B2 | 5/2011 | Francoeur et al. |
| 7,951,126 B2 | 5/2011 | Nanjyo et al. |
| 7,982,091 B2 | 7/2011 | Konawa et al. |
| 7,993,319 B2 | 8/2011 | Sperl |
| 8,017,827 B2 | 9/2011 | Hundorf et al. |
| 8,029,486 B2 | 10/2011 | Nakajima et al. |
| 8,034,991 B2 | 10/2011 | Bruzadin et al. |
| 8,039,684 B2 | 10/2011 | Guidotti et al. |
| 8,052,454 B2 | 11/2011 | Polnyi et al. |
| 8,057,620 B2 | 11/2011 | Perego et al. |
| 8,109,915 B2 | 2/2012 | Shimoe et al. |
| 8,133,212 B2 | 3/2012 | Takada et al. |
| 8,148,598 B2 | 4/2012 | Tsang et al. |
| 8,163,124 B2 | 4/2012 | Moriura et al. |
| 8,173,858 B2 | 5/2012 | Kuroda et al. |
| 8,178,747 B2 | 5/2012 | Venturino et al. |
| 8,183,430 B2 | 5/2012 | Hakansson et al. |
| 8,186,296 B2 | 5/2012 | Brown et al. |
| 8,187,240 B2 | 5/2012 | Busam et al. |
| 8,198,506 B2 | 6/2012 | Venturino et al. |
| 8,211,815 B2 | 7/2012 | Baker |
| 8,236,715 B2 | 8/2012 | Schmidt et al. |
| 8,237,012 B2 | 8/2012 | Miyama et al. |
| 8,246,594 B2 | 8/2012 | Sperl |
| 8,258,367 B2 | 9/2012 | Lawson et al. |
| 8,268,424 B1 | 9/2012 | Suzuki et al. |
| 8,273,943 B2 | 9/2012 | Noda et al. |
| 8,283,516 B2 | 10/2012 | Litvay |
| 8,317,766 B2 | 11/2012 | Naoto et al. |
| 8,317,768 B2 | 11/2012 | Larsson |
| 8,319,005 B2 | 11/2012 | Becker et al. |
| 8,343,123 B2 | 1/2013 | Noda et al. |
| 8,343,296 B2 | 1/2013 | Blessing et al. |
| 8,360,977 B2 | 1/2013 | Marttila |
| 8,361,047 B2 | 1/2013 | Mukai et al. |
| 8,377,025 B2 | 2/2013 | Nakajima et al. |
| 8,450,555 B2 | 5/2013 | Nhan et al. |
| 8,496,637 B2 | 7/2013 | Hundorf et al. |
| 8,519,213 B2 | 8/2013 | Venturino et al. |
| 8,524,355 B2 | 9/2013 | Nakaoka |
| 8,552,252 B2 | 10/2013 | Hundorf et al. |
| 8,568,566 B2 | 10/2013 | Jackels et al. |
| 8,581,019 B2 | 11/2013 | Carlucci et al. |
| 8,603,058 B2 | 12/2013 | Sperl et al. |
| 8,604,270 B2 | 12/2013 | Venturino et al. |
| 8,633,347 B2 | 1/2014 | Bianco et al. |
| 8,674,170 B2 | 3/2014 | Busam et al. |
| 8,766,031 B2 | 7/2014 | Becker et al. |
| 8,772,570 B2 | 7/2014 | Kawakami et al. |
| 8,785,715 B2 | 7/2014 | Wright et al. |
| 8,791,318 B2 | 7/2014 | Becker et al. |
| 2001/0007065 A1 | 7/2001 | Blanchard |
| 2001/0008964 A1 | 7/2001 | Kurata et al. |
| 2001/0016548 A1 | 8/2001 | Kugler et al. |
| 2001/0020157 A1 | 9/2001 | Mizutani et al. |
| 2001/0037101 A1 | 11/2001 | Allan et al. |
| 2001/0044610 A1 | 11/2001 | Kim et al. |
| 2002/0007167 A1 | 1/2002 | Dan et al. |
| 2002/0007169 A1 | 1/2002 | Graef et al. |
| 2002/0016122 A1 | 2/2002 | Curro et al. |
| 2002/0016579 A1 | 2/2002 | Stenberg |
| 2002/0045881 A1 | 4/2002 | Kusibojoska et al. |
| 2002/0056516 A1 | 5/2002 | Ochi |
| 2002/0062112 A1 | 5/2002 | Mizutani |
| 2002/0062116 A1 | 5/2002 | Mizutani et al. |
| 2002/0065498 A1 | 5/2002 | Ohashi et al. |
| 2002/0072471 A1 | 6/2002 | Ikeuchi et al. |
| 2002/0082575 A1 | 6/2002 | Dan et al. |
| 2002/0087139 A1 | 7/2002 | Popp et al. |
| 2002/0102392 A1 | 8/2002 | Fish et al. |
| 2002/0115969 A1 | 8/2002 | Maeda et al. |
| 2002/0123728 A1 | 9/2002 | Graef et al. |
| 2002/0151634 A1 | 10/2002 | Rohrbaugh et al. |
| 2002/0151861 A1 | 10/2002 | Klemp et al. |
| 2002/0173767 A1 | 11/2002 | Popp et al. |
| 2002/0192366 A1 | 12/2002 | Cramer et al. |
| 2002/0197695 A1 | 12/2002 | Glucksmann et al. |
| 2003/0036741 A1 | 2/2003 | Abba et al. |
| 2003/0078553 A1 | 4/2003 | Wada et al. |
| 2003/0084983 A1 | 5/2003 | Rangachari et al. |
| 2003/0088223 A1 | 5/2003 | Vogt et al. |
| 2003/0105190 A1 | 6/2003 | Diehl et al. |
| 2003/0114816 A1 | 6/2003 | Underhill |
| 2003/0114818 A1 | 6/2003 | Benecke et al. |
| 2003/0115969 A1 | 6/2003 | Koyano et al. |
| 2003/0120235 A1 | 6/2003 | Boulanger |
| 2003/0135181 A1 | 7/2003 | Chen et al. |
| 2003/0135182 A1 | 7/2003 | Woon et al. |
| 2003/0139712 A1 | 7/2003 | Dodge |
| 2003/0139715 A1 | 7/2003 | Dodge |
| 2003/0139718 A1 | 7/2003 | Graef |
| 2003/0144642 A1 | 7/2003 | Dopps |
| 2003/0144644 A1 | 7/2003 | Murai et al. |
| 2003/0148684 A1 | 8/2003 | Cramer et al. |
| 2003/0148694 A1 | 8/2003 | Ghiam |
| 2003/0167045 A1 | 9/2003 | Graef |
| 2003/0171727 A1 | 9/2003 | Graef |
| 2003/0208175 A1 | 11/2003 | Gross |
| 2003/0225385 A1 | 12/2003 | Glaug |
| 2003/0233082 A1 | 12/2003 | Kline et al. |
| 2003/0236512 A1 | 12/2003 | Baker |
| 2004/0019338 A1 | 1/2004 | Litvay et al. |
| 2004/0022998 A1 | 2/2004 | Miyamoto et al. |
| 2004/0033750 A1 | 2/2004 | Everett |
| 2004/0063367 A1 | 4/2004 | Dodge |
| 2004/0064115 A1 | 4/2004 | Arora |
| 2004/0064116 A1 | 4/2004 | Arora |
| 2004/0064125 A1 | 4/2004 | Justmann et al. |
| 2004/0065420 A1 | 4/2004 | Graef |
| 2004/0082928 A1 | 4/2004 | Pesce et al. |
| 2004/0097895 A1 | 5/2004 | Busam et al. |
| 2004/0122411 A1 | 6/2004 | Hancock-Cooke |
| 2004/0127871 A1 | 7/2004 | Odorzynski |
| 2004/0127872 A1 | 7/2004 | Petryk |
| 2004/0134596 A1 | 7/2004 | Rosati et al. |
| 2004/0138633 A1 | 7/2004 | Mishima et al. |
| 2004/0147890 A1 | 7/2004 | Nakahata et al. |
| 2004/0158212 A1 | 8/2004 | Ponomarenko et al. |
| 2004/0162536 A1 | 8/2004 | Becker et al. |
| 2004/0167486 A1 | 8/2004 | Busam et al. |
| 2004/0167489 A1 | 8/2004 | Kellenberger et al. |

(56) References Cited

U.S. PATENT DOCUMENTS

| | | |
|---|---|---|
| 2004/0193127 A1 | 9/2004 | Hansson et al. |
| 2004/0215160 A1 | 10/2004 | Chmielewski |
| 2004/0220541 A1 | 11/2004 | Suzuki et al. |
| 2004/0225271 A1 | 11/2004 | Datta et al. |
| 2004/0231065 A1 | 11/2004 | Daniel et al. |
| 2004/0236299 A1 | 11/2004 | Tsang et al. |
| 2004/0249355 A1 | 12/2004 | Tanio et al. |
| 2004/0260259 A1 | 12/2004 | Baker |
| 2005/0004543 A1 | 1/2005 | Schroer et al. |
| 2005/0004548 A1 | 1/2005 | Otsubo et al. |
| 2005/0008839 A1 | 1/2005 | Cramer et al. |
| 2005/0018258 A1 | 1/2005 | Miyagi et al. |
| 2005/0038401 A1 | 2/2005 | Suzuki et al. |
| 2005/0070867 A1 | 3/2005 | Beruda et al. |
| 2005/0085784 A1 | 4/2005 | LeMinh et al. |
| 2005/0090789 A1 | 4/2005 | Graef et al. |
| 2005/0101929 A1 | 5/2005 | Waksmundzki et al. |
| 2005/0137543 A1 | 6/2005 | Underhill et al. |
| 2005/0148258 A1 | 7/2005 | Chakravarty et al. |
| 2005/0148990 A1 | 7/2005 | Shimoe et al. |
| 2005/0154363 A1 | 7/2005 | Minato et al. |
| 2005/0159720 A1 | 7/2005 | Gentilcore et al. |
| 2005/0165208 A1 | 7/2005 | Popp et al. |
| 2005/0171499 A1 | 8/2005 | Nigam et al. |
| 2005/0176910 A1 | 8/2005 | Jaworek et al. |
| 2005/0203475 A1 | 9/2005 | LaVon et al. |
| 2005/0215752 A1 | 9/2005 | Popp et al. |
| 2005/0229543 A1 | 10/2005 | Tippey |
| 2005/0245684 A1 | 11/2005 | Daniel et al. |
| 2005/0288645 A1 | 12/2005 | LaVon |
| 2005/0288646 A1 | 12/2005 | LaVon |
| 2006/0004334 A1 | 1/2006 | Schlinz et al. |
| 2006/0021695 A1 | 2/2006 | Blessing et al. |
| 2006/0024433 A1 | 2/2006 | Blessing et al. |
| 2006/0069371 A1 | 3/2006 | Ohashi et al. |
| 2006/0073969 A1 | 4/2006 | Torli et al. |
| 2006/0081348 A1 | 4/2006 | Graef |
| 2006/0129114 A1 | 6/2006 | Mason et al. |
| 2006/0142724 A1 | 6/2006 | Watanabe et al. |
| 2006/0155057 A1 | 7/2006 | Hermeling et al. |
| 2006/0155254 A1 | 7/2006 | Sanz et al. |
| 2006/0167215 A1 | 7/2006 | Hermeling et al. |
| 2006/0177647 A1 | 8/2006 | Schmidt et al. |
| 2006/0178071 A1 | 8/2006 | Schmidt et al. |
| 2006/0184146 A1 | 8/2006 | Suzuki |
| 2006/0184149 A1 | 8/2006 | Kasai et al. |
| 2006/0189954 A1 | 8/2006 | Kudo et al. |
| 2006/0202380 A1 | 9/2006 | Bentley |
| 2006/0206091 A1 | 9/2006 | Cole |
| 2006/0211828 A1 | 9/2006 | Daniel et al. |
| 2006/0240229 A1 | 10/2006 | Ehrnsperger et al. |
| 2006/0264860 A1 | 11/2006 | Beck |
| 2006/0264861 A1 | 11/2006 | LaVon et al. |
| 2007/0027436 A1 | 2/2007 | Nakagawa et al. |
| 2007/0032770 A1 | 2/2007 | LaVon et al. |
| 2007/0043191 A1 | 2/2007 | Hermeling et al. |
| 2007/0043330 A1 | 2/2007 | Lankhof et al. |
| 2007/0073253 A1 | 3/2007 | Miyama et al. |
| 2007/0078422 A1 | 4/2007 | Glaug et al. |
| 2007/0088308 A1 | 4/2007 | Ehrnsperger et al. |
| 2007/0093164 A1 | 4/2007 | Nakaoka |
| 2007/0093767 A1 | 4/2007 | Carlucci et al. |
| 2007/0100307 A1 | 5/2007 | Nomoto et al. |
| 2007/0118087 A1 | 5/2007 | Flohr et al. |
| 2007/0123834 A1 | 5/2007 | McDowall et al. |
| 2007/0156108 A1 | 7/2007 | Becker et al. |
| 2007/0156110 A1 | 7/2007 | Thyfault |
| 2007/0167928 A1 | 7/2007 | Becker et al. |
| 2007/0179464 A1 | 8/2007 | Becker et al. |
| 2007/0179469 A1 | 8/2007 | Takahashi et al. |
| 2007/0191798 A1 | 8/2007 | Glaug |
| 2007/0219521 A1 | 9/2007 | Hird et al. |
| 2007/0219523 A1 | 9/2007 | Bruun et al. |
| 2007/0244455 A1 | 10/2007 | Hansson et al. |
| 2007/0246147 A1 | 10/2007 | Venturino et al. |
| 2007/0282288 A1 | 12/2007 | Noda et al. |
| 2007/0282290 A1 | 12/2007 | Cole |
| 2007/0282291 A1 | 12/2007 | Cole |
| 2008/0027402 A1 | 1/2008 | Schmidt et al. |
| 2008/0032035 A1 | 2/2008 | Schmidt et al. |
| 2008/0091159 A1 | 4/2008 | Carlucci et al. |
| 2008/0119810 A1 | 5/2008 | Kuroda et al. |
| 2008/0125735 A1 | 5/2008 | Busam et al. |
| 2008/0221538 A1 | 9/2008 | Zhao et al. |
| 2008/0221539 A1 | 9/2008 | Zhao et al. |
| 2008/0228158 A1 | 9/2008 | Sue et al. |
| 2008/0262459 A1 | 10/2008 | Kamoto et al. |
| 2008/0268194 A1 | 10/2008 | Kim et al. |
| 2008/0274227 A1 | 11/2008 | Boatman et al. |
| 2008/0281287 A1 | 11/2008 | Marcelo et al. |
| 2008/0294140 A1 | 11/2008 | Ecker et al. |
| 2008/0312618 A1 | 12/2008 | Hundorf et al. |
| 2008/0312619 A1 | 12/2008 | Ashton et al. |
| 2008/0312620 A1 | 12/2008 | Ashton et al. |
| 2008/0312621 A1 | 12/2008 | Hundorf et al. |
| 2008/0312622 A1 | 12/2008 | Hundorf et al. |
| 2008/0312623 A1 | 12/2008 | Hundorf et al. |
| 2008/0312624 A1 | 12/2008 | Hundorf et al. |
| 2008/0312625 A1 | 12/2008 | Hundorf et al. |
| 2008/0312627 A1 | 12/2008 | Takeuchi et al. |
| 2008/0312628 A1 | 12/2008 | Hundorf et al. |
| 2009/0023848 A1 | 1/2009 | Ahmed et al. |
| 2009/0056867 A1 | 3/2009 | Moriura et al. |
| 2009/0062760 A1 | 3/2009 | Wright et al. |
| 2009/0112173 A1 | 4/2009 | Bissah et al. |
| 2009/0112175 A1 | 4/2009 | Bissah et al. |
| 2009/0157022 A1 | 6/2009 | MacDonald |
| 2009/0192035 A1 | 7/2009 | Stueven et al. |
| 2009/0240220 A1 | 9/2009 | Macdonald et al. |
| 2009/0247977 A1 | 10/2009 | Takeuchi et al. |
| 2009/0258994 A1 | 10/2009 | Stueven et al. |
| 2009/0270825 A1 | 10/2009 | Wciorka et al. |
| 2009/0298963 A1 | 12/2009 | Matsumoto et al. |
| 2009/0299312 A1 | 12/2009 | Macdonald |
| 2009/0306618 A1 | 12/2009 | Kudo et al. |
| 2009/0318884 A1 | 12/2009 | Meyer et al. |
| 2010/0051166 A1 | 3/2010 | Hundorf et al. |
| 2010/0062165 A1 | 3/2010 | Suzuki et al. |
| 2010/0062934 A1 | 3/2010 | Suzuki et al. |
| 2010/0063470 A1 | 3/2010 | Suzuki et al. |
| 2010/0068520 A1 | 3/2010 | Stueven et al. |
| 2010/0100065 A1 | 4/2010 | Bianco et al. |
| 2010/0115237 A1 | 5/2010 | Brewer et al. |
| 2010/0121296 A1 | 5/2010 | Noda et al. |
| 2010/0137773 A1 | 6/2010 | Gross |
| 2010/0137823 A1 | 6/2010 | Corneliusson et al. |
| 2010/0198179 A1 | 8/2010 | Noda et al. |
| 2010/0228210 A1 | 9/2010 | Busam et al. |
| 2010/0241097 A1 | 9/2010 | Nigam et al. |
| 2010/0262099 A1 | 10/2010 | Klofta |
| 2010/0274208 A1 | 10/2010 | Gabrielii et al. |
| 2010/0274210 A1 | 10/2010 | Noda et al. |
| 2010/0312208 A1 | 12/2010 | Bond et al. |
| 2010/0324521 A1 | 12/2010 | Mukai et al. |
| 2010/0324523 A1 | 12/2010 | Mukai et al. |
| 2011/0041999 A1 | 2/2011 | Hundorf et al. |
| 2011/0060303 A1 | 3/2011 | Bissah et al. |
| 2011/0066127 A1 | 3/2011 | Kuwano et al. |
| 2011/0071486 A1 | 3/2011 | Harada et al. |
| 2011/0092944 A1 | 4/2011 | Sagisaka et al. |
| 2011/0112498 A1 | 5/2011 | Nhan et al. |
| 2011/0125120 A1 | 5/2011 | Nishitani et al. |
| 2011/0130732 A1 | 6/2011 | Jackels et al. |
| 2011/0130737 A1 | 6/2011 | Sagisaka et al. |
| 2011/0137276 A1 | 6/2011 | Yoshikawa et al. |
| 2011/0144602 A1 | 6/2011 | Long et al. |
| 2011/0144604 A1 | 6/2011 | Noda et al. |
| 2011/0144606 A1 | 6/2011 | Nandrea et al. |
| 2011/0152813 A1 | 6/2011 | Ellingson |
| 2011/0166540 A1 | 7/2011 | Yang |
| 2011/0172630 A1 | 7/2011 | Nomoto et al. |
| 2011/0174430 A1 | 7/2011 | Zhao et al. |
| 2011/0208147 A1 | 8/2011 | Kawakami et al. |
| 2011/0250413 A1 | 10/2011 | Lu et al. |

(56) References Cited

U.S. PATENT DOCUMENTS

| | | |
|---|---|---|
| 2011/0268932 A1 | 11/2011 | Catalan et al. |
| 2011/0274834 A1 | 11/2011 | Brown et al. |
| 2011/0288513 A1 | 11/2011 | Hundorf et al. |
| 2011/0288514 A1 | 11/2011 | Kuroda et al. |
| 2011/0319846 A1 | 12/2011 | Rinnert et al. |
| 2011/0319848 A1 | 12/2011 | Mckiernan et al. |
| 2011/0319851 A1 | 12/2011 | Kudo et al. |
| 2012/0004633 A1 | 1/2012 | Marcelo et al. |
| 2012/0016326 A1 | 1/2012 | Brennan et al. |
| 2012/0022479 A1 | 1/2012 | Cotton |
| 2012/0035566 A1 | 2/2012 | Sagisaka et al. |
| 2012/0035576 A1 | 2/2012 | Ichikawa et al. |
| 2012/0064792 A1 | 3/2012 | Bauduin |
| 2012/0071848 A1 | 3/2012 | Zhang et al. |
| 2012/0165771 A1 | 6/2012 | Ruman et al. |
| 2012/0165776 A1 | 6/2012 | McGregor et al. |
| 2012/0175056 A1 | 7/2012 | Tsang |
| 2012/0184934 A1 | 7/2012 | Venturino |
| 2012/0232514 A1 | 9/2012 | Baker |
| 2012/0238977 A1 | 9/2012 | Oku et al. |
| 2012/0253306 A1 | 10/2012 | Otsubo et al. |
| 2012/0256750 A1 | 10/2012 | Novak |
| 2012/0271262 A1 | 10/2012 | Venturino |
| 2012/0312491 A1 | 12/2012 | Jackels et al. |
| 2012/0316046 A1 | 12/2012 | Jackels et al. |
| 2012/0316523 A1 | 12/2012 | Hippe et al. |
| 2012/0316526 A1 | 12/2012 | Rosati et al. |
| 2012/0316527 A1 | 12/2012 | Rosati et al. |
| 2012/0316528 A1 | 12/2012 | Kreuzer et al. |
| 2012/0316529 A1 | 12/2012 | Kreuzer et al. |
| 2012/0323195 A1 | 12/2012 | Ehrnsperger et al. |
| 2012/0323201 A1 | 12/2012 | Bissah et al. |
| 2012/0323202 A1 | 12/2012 | Bissah et al. |
| 2013/0035656 A1 | 2/2013 | Moriya et al. |
| 2013/0041334 A1 | 2/2013 | Prioleau |
| 2013/0211354 A1 | 8/2013 | Tsuji et al. |
| 2013/0218115 A1 | 8/2013 | Katsuragawa et al. |
| 2013/0226119 A1 | 8/2013 | Katsuragawa et al. |
| 2013/0226120 A1 | 8/2013 | Van de Maele |
| 2014/0005622 A1 | 1/2014 | Wirtz et al. |
| 2014/0005623 A1 | 1/2014 | Wirtz et al. |
| 2014/0027066 A1 | 1/2014 | Jackels et al. |
| 2014/0039437 A1 | 1/2014 | Valero Lafuente |
| 2014/0045683 A1 | 2/2014 | Loick et al. |
| 2014/0135726 A1 | 5/2014 | Busam et al. |
| 2014/0142531 A1 | 5/2014 | Sasayama et al. |
| 2014/0163500 A1 | 6/2014 | Roe et al. |
| 2014/0163501 A1 | 6/2014 | Ehrnsperger et al. |
| 2014/0163502 A1 | 6/2014 | Arizti et al. |
| 2014/0163503 A1 | 6/2014 | Arizti et al. |
| 2014/0163506 A1 | 6/2014 | Roe et al. |
| 2014/0163511 A1 | 6/2014 | Roe et al. |
| 2014/0324007 A1 | 10/2014 | Hundorf et al. |
| 2014/0324008 A1 | 10/2014 | Hundorf et al. |

FOREIGN PATENT DOCUMENTS

| | | |
|---|---|---|
| CA | 2308961 | 11/2000 |
| CA | 2487027 | 12/2003 |
| CA | 2561521 | 3/2007 |
| CA | 2630713 | 11/2008 |
| CA | 2636673 | 1/2009 |
| CA | 2712563 | 8/2010 |
| CA | 2702001 | 10/2010 |
| CN | 1238171 A | 12/1999 |
| CN | 2362468 Y | 2/2000 |
| CN | 2527254 Y | 12/2002 |
| CN | 2535020 Y | 2/2003 |
| CN | 2548609 Y | 5/2003 |
| CN | 1539391 | 10/2004 |
| CN | 1939242 | 4/2007 |
| CN | 101292930 | 10/2008 |
| CN | 201263750 | 7/2009 |
| CN | 201591689 | 9/2010 |
| CN | 201855366 U | 6/2011 |
| DE | 3205931 C2 | 9/1983 |
| DE | 3608114 A1 | 9/1987 |
| DE | 19732499 | 2/1999 |
| DE | 10204937 A1 | 8/2003 |
| EP | 083022 | 7/1983 |
| EP | 0 149 880 A2 | 7/1985 |
| EP | 149880 | 7/1985 |
| EP | 0 203 289 A2 | 12/1986 |
| EP | 0206208 | 12/1986 |
| EP | 209561 B1 | 1/1987 |
| EP | 297411 B1 | 1/1989 |
| EP | 304957 | 3/1989 |
| EP | 374542 | 6/1990 |
| EP | 394274 | 10/1990 |
| EP | 0403832 | 12/1990 |
| EP | 481322 B1 | 4/1992 |
| EP | 530438 | 3/1993 |
| EP | 547847 | 6/1993 |
| EP | 555346 | 8/1993 |
| EP | 559476 | 9/1993 |
| EP | 591647 B2 | 4/1994 |
| EP | 597273 B1 | 5/1994 |
| EP | 601610 B2 | 6/1994 |
| EP | 632068 | 1/1995 |
| EP | 0 640 330 A1 | 3/1995 |
| EP | 0668066 | 9/1995 |
| EP | 685214 | 12/1995 |
| EP | 687453 | 12/1995 |
| EP | 0689817 | 1/1996 |
| EP | 0691133 | 1/1996 |
| EP | 724418 | 8/1996 |
| EP | 725613 | 8/1996 |
| EP | 725615 | 8/1996 |
| EP | 725616 | 8/1996 |
| EP | 758543 | 2/1997 |
| EP | 0761194 | 3/1997 |
| EP | 769284 | 4/1997 |
| EP | 0781537 | 7/1997 |
| EP | 783877 B1 | 7/1997 |
| EP | 787472 | 8/1997 |
| EP | 788874 B1 | 8/1997 |
| EP | 796068 | 9/1997 |
| EP | 799004 | 10/1997 |
| EP | 822794 B1 | 2/1998 |
| EP | 826351 | 3/1998 |
| EP | 844861 | 6/1998 |
| EP | 863733 | 9/1998 |
| EP | 971751 | 9/1998 |
| EP | 875224 A1 | 11/1998 |
| EP | 880955 | 12/1998 |
| EP | 891758 | 1/1999 |
| EP | 0893115 | 1/1999 |
| EP | 904755 | 3/1999 |
| EP | 0916327 | 5/1999 |
| EP | 925769 A2 | 6/1999 |
| EP | 933074 | 8/1999 |
| EP | 937736 | 8/1999 |
| EP | 941157 | 9/1999 |
| EP | 947549 | 10/1999 |
| EP | 951887 B1 | 10/1999 |
| EP | 0951890 | 10/1999 |
| EP | 2295493 | 10/1999 |
| EP | 2305749 | 10/1999 |
| EP | 2330152 | 10/1999 |
| EP | 953326 | 11/1999 |
| EP | 0978263 A1 | 2/2000 |
| EP | 985397 B1 | 3/2000 |
| EP | 1005847 | 6/2000 |
| EP | 1008333 | 6/2000 |
| EP | 1013252 B1 | 6/2000 |
| EP | 1018999 | 7/2000 |
| EP | 1019002 B1 | 7/2000 |
| EP | 1019003 B1 | 7/2000 |
| EP | 1022008 | 7/2000 |
| EP | 1023884 | 8/2000 |
| EP | 1053729 | 11/2000 |
| EP | 1059072 A2 | 12/2000 |
| EP | 1063954 | 1/2001 |

(56) References Cited

FOREIGN PATENT DOCUMENTS

| | | |
|---|---|---|
| EP | 1071388 | 1/2001 |
| EP | 1078618 | 2/2001 |
| EP | 1 088 537 A2 | 4/2001 |
| EP | 1116479 A2 | 7/2001 |
| EP | 1132069 | 9/2001 |
| EP | 1173128 | 1/2002 |
| EP | 1175194 B1 | 1/2002 |
| EP | 1184018 | 3/2002 |
| EP | 1192312 B1 | 4/2002 |
| EP | 1196122 B2 | 4/2002 |
| EP | 1199059 | 4/2002 |
| EP | 1199327 | 4/2002 |
| EP | 1208824 | 5/2002 |
| EP | 0793469 | 6/2002 |
| EP | 1210925 | 6/2002 |
| EP | 1224922 | 7/2002 |
| EP | 1225857 | 7/2002 |
| EP | 1262531 A1 | 12/2002 |
| EP | 1263374 B1 | 12/2002 |
| EP | 1275358 | 1/2003 |
| EP | 1275361 | 1/2003 |
| EP | 1293187 | 3/2003 |
| EP | 1304986 B1 | 5/2003 |
| EP | 1332742 B1 | 8/2003 |
| EP | 1339368 | 9/2003 |
| EP | 1374817 | 1/2004 |
| EP | 1388334 | 2/2004 |
| EP | 1402863 | 3/2004 |
| EP | 1 447 006 A | 8/2004 |
| EP | 962208 | 8/2004 |
| EP | 1447067 | 8/2004 |
| EP | 1460987 | 9/2004 |
| EP | 963749 | 11/2004 |
| EP | 1495739 | 1/2005 |
| EP | 1524955 | 4/2005 |
| EP | 1920743 | 4/2005 |
| EP | 1541103 | 6/2005 |
| EP | 1551344 | 7/2005 |
| EP | 1586289 | 10/2005 |
| EP | 1588723 | 10/2005 |
| EP | 1605882 | 12/2005 |
| EP | 1609448 | 12/2005 |
| EP | 1 621 167 A | 2/2006 |
| EP | 1621166 | 2/2006 |
| EP | 1632206 | 3/2006 |
| EP | 1642556 | 4/2006 |
| EP | 1656162 | 5/2006 |
| EP | 1669046 | 6/2006 |
| EP | 1688114 | 8/2006 |
| EP | 2314265 | 8/2006 |
| EP | 1723939 | 11/2006 |
| EP | 1738727 | 1/2007 |
| EP | 1754461 | 2/2007 |
| EP | 1787611 | 5/2007 |
| EP | 1813238 | 8/2007 |
| EP | 2008626 | 12/2008 |
| EP | 2055279 A1 | 5/2009 |
| EP | 2093049 | 8/2009 |
| EP | 2130522 | 12/2009 |
| EP | 2444046 | 4/2012 |
| EP | 2532328 | 12/2012 |
| EP | 2532329 A1 | 12/2012 |
| EP | 2532332 A1 | 12/2012 |
| EP | 2679210 A1 | 1/2014 |
| EP | 2740449 | 6/2014 |
| EP | 2740450 | 6/2014 |
| EP | 2740452 | 6/2014 |
| ES | 2213491 | 8/2004 |
| FR | 2566631 | 1/1986 |
| FR | 2612770 | 9/1988 |
| FR | 2810234 | 12/2001 |
| GB | 1333081 A | 8/1971 |
| GB | 1307441 | 2/1973 |
| GB | 1513055 | 6/1978 |
| GB | 2101468 | 1/1983 |
| GB | 2170108 | 7/1986 |
| GB | 2262873 | 7/1993 |
| GB | 2288540 A | 6/1994 |
| GB | 2354449 | 3/2001 |
| GB | 2452260 A | 10/2007 |
| GR | 851769 | 11/1985 |
| IN | 0984/1999 | 10/2005 |
| IN | 212479 B | 3/2007 |
| IN | 208543 B | 8/2007 |
| IN | 0980/2009 | 6/2009 |
| JP | 03224481 B2 | 10/1991 |
| JP | 04122256 | 4/1992 |
| JP | 06-269475 | 9/1994 |
| JP | 10328232 | 12/1998 |
| JP | 11033056 A | 2/1999 |
| JP | 11318980 | 11/1999 |
| JP | 2000232985 | 8/2000 |
| JP | 2000-238161 A | 9/2000 |
| JP | 2001037810 | 2/2001 |
| JP | 2001046435 A | 2/2001 |
| JP | 2001120597 | 5/2001 |
| JP | 2001-158074 A | 6/2001 |
| JP | 2001178768 A | 7/2001 |
| JP | 2001198157 | 7/2001 |
| JP | 2001224626 A | 8/2001 |
| JP | 03420481 B2 | 11/2001 |
| JP | 2001353174 A | 12/2001 |
| JP | 2002-052042 A | 2/2002 |
| JP | 2002-113800 | 4/2002 |
| JP | 2002165832 | 6/2002 |
| JP | 2002165836 | 6/2002 |
| JP | 2002272769 A | 9/2002 |
| JP | 2002-325799 | 11/2002 |
| JP | 2002325792 A | 11/2002 |
| JP | 2002369841 A | 12/2002 |
| JP | 2003153955 A | 5/2003 |
| JP | 2003265524 A | 9/2003 |
| JP | 2003275237 | 9/2003 |
| JP | 2004089269 | 3/2004 |
| JP | 03566012 B2 | 6/2004 |
| JP | 03568146 B2 | 6/2004 |
| JP | 03616077 B2 | 11/2004 |
| JP | 2004337314 A | 12/2004 |
| JP | 2004337385 A | 12/2004 |
| JP | 2004350864 | 12/2004 |
| JP | 03640475 B2 | 1/2005 |
| JP | 2005000312 A | 1/2005 |
| JP | 03660816 B2 | 3/2005 |
| JP | 03676219 B2 | 5/2005 |
| JP | 03688403 B2 | 6/2005 |
| JP | 03705943 B2 | 8/2005 |
| JP | 03719819 B2 | 9/2005 |
| JP | 03724963 B2 | 9/2005 |
| JP | 03725008 B2 | 9/2005 |
| JP | 03737376 B2 | 11/2005 |
| JP | 2006014792 A | 1/2006 |
| JP | 03781617 B2 | 3/2006 |
| JP | 2006-110329 A | 4/2006 |
| JP | 03801449 B2 | 5/2006 |
| JP | 2006116036 A | 5/2006 |
| JP | 03850102 B2 | 9/2006 |
| JP | 03850207 B2 | 9/2006 |
| JP | 03856941 B2 | 9/2006 |
| JP | 03868628 B2 | 10/2006 |
| JP | 03874499 B2 | 11/2006 |
| JP | 03877702 B2 | 11/2006 |
| JP | 2006325639 A | 12/2006 |
| JP | 2006346021 | 12/2006 |
| JP | 03904356 B2 | 1/2007 |
| JP | 2007007455 A | 1/2007 |
| JP | 2007007456 A | 1/2007 |
| JP | 03926042 B2 | 3/2007 |
| JP | 03934855 B2 | 3/2007 |
| JP | 2007089906 A | 4/2007 |
| JP | 2007105198 A | 4/2007 |
| JP | 2007152033 A | 6/2007 |
| JP | 03986210 B2 | 7/2007 |
| JP | 03986222 B2 | 7/2007 |
| JP | 2007167453 | 7/2007 |

(56) References Cited

FOREIGN PATENT DOCUMENTS

| | | |
|---|---|---|
| JP | 2007175515 A | 7/2007 |
| JP | 2007195665 A | 8/2007 |
| JP | 2007267763 A | 10/2007 |
| JP | 2007275491 A | 10/2007 |
| JP | 04035341 B2 | 11/2007 |
| JP | 04058281 B2 | 12/2007 |
| JP | 04061086 B2 | 12/2007 |
| JP | 04092319 B2 | 3/2008 |
| JP | 2008080150 A | 4/2008 |
| JP | 2008093289 A | 4/2008 |
| JP | 04124322 B2 | 5/2008 |
| JP | 2008119081 A | 5/2008 |
| JP | 2008136739 A | 6/2008 |
| JP | 2008136877 A | 6/2008 |
| JP | 04148594 B2 | 7/2008 |
| JP | 04148620 B2 | 7/2008 |
| JP | 2008154606 A | 7/2008 |
| JP | 04162609 B2 | 8/2008 |
| JP | 04162637 B2 | 8/2008 |
| JP | 04166923 B2 | 8/2008 |
| JP | 04167406 B2 | 8/2008 |
| JP | 04173723 B2 | 8/2008 |
| JP | 04190675 B2 | 9/2008 |
| JP | 04190693 B2 | 9/2008 |
| JP | 04208338 B2 | 10/2008 |
| JP | 2008246089 | 10/2008 |
| JP | 04230971 B2 | 12/2008 |
| JP | 2008295475 A | 12/2008 |
| JP | 2008295713 A | 12/2008 |
| JP | 04261593 B2 | 2/2009 |
| JP | 2009112590 | 5/2009 |
| JP | 04322228 B2 | 6/2009 |
| JP | 2009136601 | 6/2009 |
| JP | 2009142401 A | 7/2009 |
| JP | 2009201878 A | 9/2009 |
| JP | 04392936 B2 | 10/2009 |
| JP | 2009232987 A | 10/2009 |
| JP | 2009261777 A | 11/2009 |
| JP | 2009291473 A | 12/2009 |
| JP | 2009297048 A | 12/2009 |
| JP | 2010017342 | 1/2010 |
| JP | 04458702 B2 | 2/2010 |
| JP | 04459013 B2 | 2/2010 |
| JP | 2010022560 | 2/2010 |
| JP | 04481325 B2 | 3/2010 |
| JP | 2010051654 A | 3/2010 |
| JP | 2010063814 A | 3/2010 |
| JP | 2010063944 A | 3/2010 |
| JP | 04492957 B2 | 4/2010 |
| JP | 2010068954 A | 4/2010 |
| JP | 2010075462 A | 4/2010 |
| JP | 2010082059 A | 4/2010 |
| JP | 2010104545 A | 5/2010 |
| JP | 2010104547 A | 5/2010 |
| JP | 2010110535 A | 5/2010 |
| JP | 2010119454 A | 6/2010 |
| JP | 2010119605 A | 6/2010 |
| JP | 2010119743 A | 6/2010 |
| JP | 2010131131 A | 6/2010 |
| JP | 2010131132 A | 6/2010 |
| JP | 2010131206 | 6/2010 |
| JP | 2010131297 A | 6/2010 |
| JP | 2010136917 A | 6/2010 |
| JP | 2010136973 A | 6/2010 |
| JP | 04540563 B2 | 7/2010 |
| JP | 04587947 B2 | 9/2010 |
| JP | 2010194124 A | 9/2010 |
| JP | 2010201093 | 9/2010 |
| JP | 2010221067 | 10/2010 |
| JP | 04620299 B2 | 11/2010 |
| JP | 04627472 B2 | 11/2010 |
| JP | 04627473 B2 | 11/2010 |
| JP | 04638087 B2 | 12/2010 |
| JP | 04652626 B2 | 12/2010 |
| JP | 2010273842 A | 12/2010 |
| JP | 2010284418 A | 12/2010 |
| JP | 2011000480 A | 1/2011 |
| JP | 2011030700 | 2/2011 |
| JP | 04693574 B2 | 3/2011 |
| JP | 2011067484 A | 4/2011 |
| JP | 2011072720 A | 4/2011 |
| JP | 2011104014 | 6/2011 |
| JP | 2011104122 | 6/2011 |
| JP | 2011120661 A | 6/2011 |
| JP | 2011125360 A | 6/2011 |
| JP | 2011125537 | 6/2011 |
| JP | 04776516 B2 | 7/2011 |
| JP | 2011130797 A | 7/2011 |
| JP | 2011130799 A | 7/2011 |
| JP | 2011156032 A | 8/2011 |
| JP | 2011156070 A | 8/2011 |
| JP | 2011156254 | 8/2011 |
| JP | 04824882 B2 | 9/2011 |
| JP | 4850272 B2 | 10/2011 |
| JP | 04855533 B2 | 11/2011 |
| JP | 2011239858 | 12/2011 |
| JP | 04931572 B2 | 2/2012 |
| JP | 04937225 B2 | 3/2012 |
| JP | 04953618 B2 | 3/2012 |
| JP | 04969437 B2 | 4/2012 |
| JP | 04969640 B2 | 4/2012 |
| JP | 4971491 B2 | 4/2012 |
| JP | 04974524 B2 | 4/2012 |
| JP | 04979780 B2 | 4/2012 |
| JP | 05016020 B2 | 6/2012 |
| JP | 05027364 B2 | 6/2012 |
| JP | 05031082 B2 | 7/2012 |
| JP | 05042351 B2 | 7/2012 |
| JP | 05043569 B2 | 7/2012 |
| JP | 05043591 B2 | 7/2012 |
| JP | 05046488 B2 | 7/2012 |
| JP | 2012125625 A | 7/2012 |
| JP | 05053765 B2 | 8/2012 |
| JP | 05070275 B2 | 8/2012 |
| JP | 05079931 B1 | 9/2012 |
| JP | 05080189 B2 | 9/2012 |
| JP | 05084442 B2 | 9/2012 |
| JP | 05084476 B2 | 9/2012 |
| JP | 5085770 B2 | 9/2012 |
| JP | 05089269 B2 | 9/2012 |
| JP | 05113146 B2 | 10/2012 |
| JP | 05129536 B2 | 11/2012 |
| JP | 05105884 B2 | 12/2012 |
| KR | 20010005620 | 1/2001 |
| KR | 20020035634 | 5/2002 |
| KR | 20080028771 | 4/2008 |
| SE | 9400916 | 3/1994 |
| SE | 9704893 | 12/1997 |
| WO | WO9015830 | 12/1990 |
| WO | WO9321237 | 10/1993 |
| WO | WO9321879 | 11/1993 |
| WO | WO9510996 | 4/1995 |
| WO | WO9511652 | 5/1995 |
| WO | WO 95/16746 A1 | 6/1995 |
| WO | WO9514453 | 6/1995 |
| WO | WO9515139 | 6/1995 |
| WO | WO9516424 | 6/1995 |
| WO | WO9519753 | 7/1995 |
| WO | WO9521596 | 8/1995 |
| WO | WO9524173 | 9/1995 |
| WO | WO9529657 | 11/1995 |
| WO | WO9532698 | 12/1995 |
| WO | WO9534329 | 12/1995 |
| WO | WO9616624 | 6/1996 |
| WO | WO9619173 | 6/1996 |
| WO | WO 97/11659 | 4/1997 |
| WO | WO9717922 | 5/1997 |
| WO | WO9816179 | 4/1998 |
| WO | WO9816180 | 4/1998 |
| WO | WO9843684 | 10/1998 |
| WO | WO9913813 | 3/1999 |
| WO | WO9934841 | 7/1999 |
| WO | WO9951178 | 10/1999 |
| WO | WO0000235 | 1/2000 |

(56) References Cited

FOREIGN PATENT DOCUMENTS

| | | |
|---|---|---|
| WO | WO0032145 | 6/2000 |
| WO | WO0059430 | 10/2000 |
| WO | WO 01/15647 | 3/2001 |
| WO | WO0126596 | 4/2001 |
| WO | WO0207663 | 1/2002 |
| WO | WO0232962 | 4/2002 |
| WO | WO 02/064877 A2 | 8/2002 |
| WO | WO02067809 | 9/2002 |
| WO | WO03009794 | 2/2003 |
| WO | WO2003039402 | 5/2003 |
| WO | WO03053297 | 7/2003 |
| WO | WO03105738 | 12/2003 |
| WO | WO2004021946 | 3/2004 |
| WO | WO2004049995 | 6/2004 |
| WO | WO 2004/071539 A3 | 8/2004 |
| WO | WO2004084784 | 10/2004 |
| WO | WO2004105664 | 12/2004 |
| WO | WO2005/018694 | 3/2005 |
| WO | WO2005087164 | 9/2005 |
| WO | WO2006104024 | 5/2006 |
| WO | WO 2006/062258 A2 | 6/2006 |
| WO | WO2006059922 | 6/2006 |
| WO | WO2006066029 | 6/2006 |
| WO | WO2006083584 | 8/2006 |
| WO | WO2006134904 | 12/2006 |
| WO | WO2006134906 | 12/2006 |
| WO | WO2007000315 | 1/2007 |
| WO | WO2007046052 | 4/2007 |
| WO | WO2007047598 | 4/2007 |
| WO | WO2007049725 | 5/2007 |
| WO | WO2007061035 | 5/2007 |
| WO | WO2007142145 | 12/2007 |
| WO | WO2007148502 | 12/2007 |
| WO | WO2008018922 | 2/2008 |
| WO | WO2008065945 | 6/2008 |
| WO | WO2008146749 | 12/2008 |
| WO | WO2008155699 | 12/2008 |
| WO | WO2009004941 | 1/2009 |
| WO | WO2009005431 | 1/2009 |
| WO | WO2009139248 | 1/2009 |
| WO | WO2009139255 | 1/2009 |
| WO | WO2009041223 | 4/2009 |
| WO | WO2009096108 | 8/2009 |
| WO | WO2009107435 | 9/2009 |
| WO | WO2009122830 | 10/2009 |
| WO | WO2009152018 | 12/2009 |
| WO | WO2009155264 | 12/2009 |
| WO | WO2009155265 | 12/2009 |
| WO | WO2010071508 | 6/2010 |
| WO | WO2010074319 | 7/2010 |
| WO | WO2010107096 | 9/2010 |
| WO | WO2010114052 | 10/2010 |
| WO | WO2010117015 | 10/2010 |
| WO | WO201153044 | 5/2011 |
| WO | WO2011118725 | 9/2011 |
| WO | WO2011118842 | 9/2011 |
| WO | WO2011145653 | 11/2011 |
| WO | WO2011150955 | 12/2011 |
| WO | WO2011163582 | 12/2011 |
| WO | WO2012002252 | 1/2012 |
| WO | WO2012014436 | 2/2012 |
| WO | WO2012042908 | 4/2012 |
| WO | WO2012043077 | 4/2012 |
| WO | WO2012043078 | 4/2012 |
| WO | WO2012052172 | 4/2012 |
| WO | WO2012043082 | 5/2012 |
| WO | WO2012067216 | 5/2012 |
| WO | WO2012073499 | 6/2012 |
| WO | WO2012074466 | 6/2012 |
| WO | WO201291016 | 7/2012 |
| WO | WO2012090508 | 7/2012 |
| WO | WO2012101934 | 8/2012 |
| WO | WO2012102034 | 8/2012 |
| WO | WO2012117824 | 9/2012 |
| WO | WO2012132460 | 10/2012 |
| WO | WO2012170778 | 12/2012 |
| WO | WO2012170779 | 12/2012 |
| WO | WO2012170781 | 12/2012 |
| WO | WO2012170808 | 12/2012 |
| WO | WO2012174026 | 12/2012 |
| WO | WO2013001788 | 1/2013 |
| WO | WO2013060733 | 5/2013 |
| WO | WO2014078247 | 5/2014 |

* cited by examiner

DISPOSABLE ABSORBENT ARTICLE WITH SUBSTANTIALLY CONTINUOUSLY DISTRIBUTED ABSORBENT PARTICULATE POLYMER MATERIAL AND METHOD

CROSS REFERENCE TO RELATED APPLICATIONS

This application claims the benefit of U.S. Provisional Application No. 60/936,102, filed on Jun. 18, 2007.

FIELD OF THE INVENTION

The present invention generally relates to an absorbent article, and more particularly to a disposable absorbent article with absorbent particulate polymer material, such as a diaper.

BACKGROUND OF THE INVENTION

Absorbent articles, such as disposable diapers, training pants, and adult incontinence undergarments, absorb and contain body exudates. They also are intended to prevent body exudates from soiling, wetting, or otherwise contaminating clothing or other articles, such as bedding, that come in contact with the wearer. A disposable absorbent article, such as a disposable diaper, may be worn for several hours in a dry state or in a urine loaded state. Accordingly, efforts have been made toward improving the fit and comfort of the absorbent article to the wearer, both when the article is dry and when the article is fully or partially loaded with liquid exudate, while maintaining or enhancing the absorbing and containing functions of the article.

Some absorbent articles, like diapers, contain an absorbent polymer material (also known as super absorbent polymer), such as an absorbent particulate polymer material. Absorbent particulate polymer material absorbs liquid and swells and may be more effective when disposed in an absorbent article in a certain pattern or arrangement intended for optimal absorbency, fit, and/or comfort. Thus, it may be desirable for absorbent particulate polymer material to remain in its intended location in an absorbent article and absorbent particulate polymer material, therefore, is desirably immobilized in the absorbent article such that the absorbent particulate polymer material remains immobilized when the absorbent article is dry and when it is wet.

In addition to being absorbent, absorbent articles, such as diapers, may desirably be thin and flexible, for ease and comfort in use and for more convenient and neat packaging and storage. Absorbent articles, which may often be used in large quantities, may also desirably be inexpensive. Some technologies of immobilizing absorbent particulate polymer material in an absorbent article add bulk to the absorbent article and thereby increase thickness, reduce flexibility, and/or increase cost of the absorbent article. Other technologies for immobilizing absorbent particulate polymer material in an absorbent article may not be as effective in maintaining immobilization when the absorbent article is in the wet state as when in the dry state. Accordingly, there remains a need for a thin, flexible, and/or inexpensive absorbent article containing absorbent particulate polymer material with enhanced immobilization of the absorbent particulate polymer material in the article in dry and wet states.

SUMMARY OF THE INVENTION

The present invention addresses one or more technical problems described above and provides a disposable absorbent article which may comprise a chassis and an absorbent core. The chassis may contain a topsheet and a backsheet. The absorbent core may be located between the topsheet and the backsheet and may include first and second absorbent layers. The first absorbent layer may include first substrate and the second absorbent layer may include a second substrate. The first and second absorbent layers may further include absorbent particulate polymer material deposited on the first and second substrates and thermoplastic adhesive material covering the absorbent particulate polymer material on the respective first and second substrates.

The first and second absorbent layers may be combined together such that at least a portion of said thermoplastic adhesive material of said first absorbent layer contacts at least a portion of the thermoplastic adhesive material of said second absorbent layer, the absorbent particulate polymer material is disposed between the first and second substrates in an absorbent particulate polymer area, and the absorbent particulate polymer material is substantially continuously distributed across the absorbent particulate polymer material area.

According to another aspect of this invention, an absorbent core as described herein above is provided.

According to yet another aspect of this invention, a method of making a disposable absorbent article is provided comprising depositing absorbent particulate polymer material on a first substrate in a first pattern to form a first absorbent layer such that the absorbent particulate polymer material is discontinuously distributed on the first substrate, depositing absorbent particulate polymer material on a second substrate in a second pattern to form a second absorbent layer such that the absorbent particulate polymer material is discontinuously distributed on the second substrate, depositing a thermoplastic layer on the absorbent particulate polymer material and the first and second substrates to cover the absorbent particulate polymer material on the first and second substrates, and combining the first and second absorbent layers together such that at least a portion of said thermoplastic adhesive material of said first absorbent layer contacts at least a portion of the thermoplastic adhesive material of said second absorbent layer, the absorbent particulate polymer material is disposed between the first and second substrates in an absorbent particulate polymer material area, and the absorbent particulate polymer material is substantially continuously distributed across the absorbent polymer material area.

Other features and advantages of the invention may be apparent from reading the following detailed description, drawings, and claims.

DETAILED DESCRIPTION OF THE INVENTION

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

"Absorbent core" means a structure typically disposed between a topsheet and backsheet of an absorbent article for absorbing and containing liquid received by the absorbent article and may comprise one or more substrates, absorbent polymer material disposed on the one or more substrates, and a thermoplastic composition on the absorbent particulate polymer material and at least a portion of the one or more substrates for immobilizing the absorbent particulate polymer material on the one or more substrates. In a multilayer absorbent core, the absorbent core may also include a cover layer. The one or more substrates and the cover layer may comprise a nonwoven. Further, the absorbent core is substantially cellulose free. The absorbent core does not include an acquisition system, a topsheet, or a backsheet of the absorbent article. In a certain embodiment, the absorbent core would consist essentially of the one or more substrates, the absorbent polymer material, the thermoplastic composition, and optionally the cover layer.

"Absorbent polymer material," "absorbent gelling material," "AGM," "superabsorbent," and "superabsorbent material" are used herein interchangeably and refer to cross linked polymeric materials that can absorb at least 5 times their weight of an aqueous 0.9% saline solution as measured using the Centrifuge Retention Capacity test (Edana 441.2-01).

"Absorbent particulate polymer material" is used herein to refer to an absorbent polymer material which is in particulate form so as to be flowable in the dry state.

Figure 8:
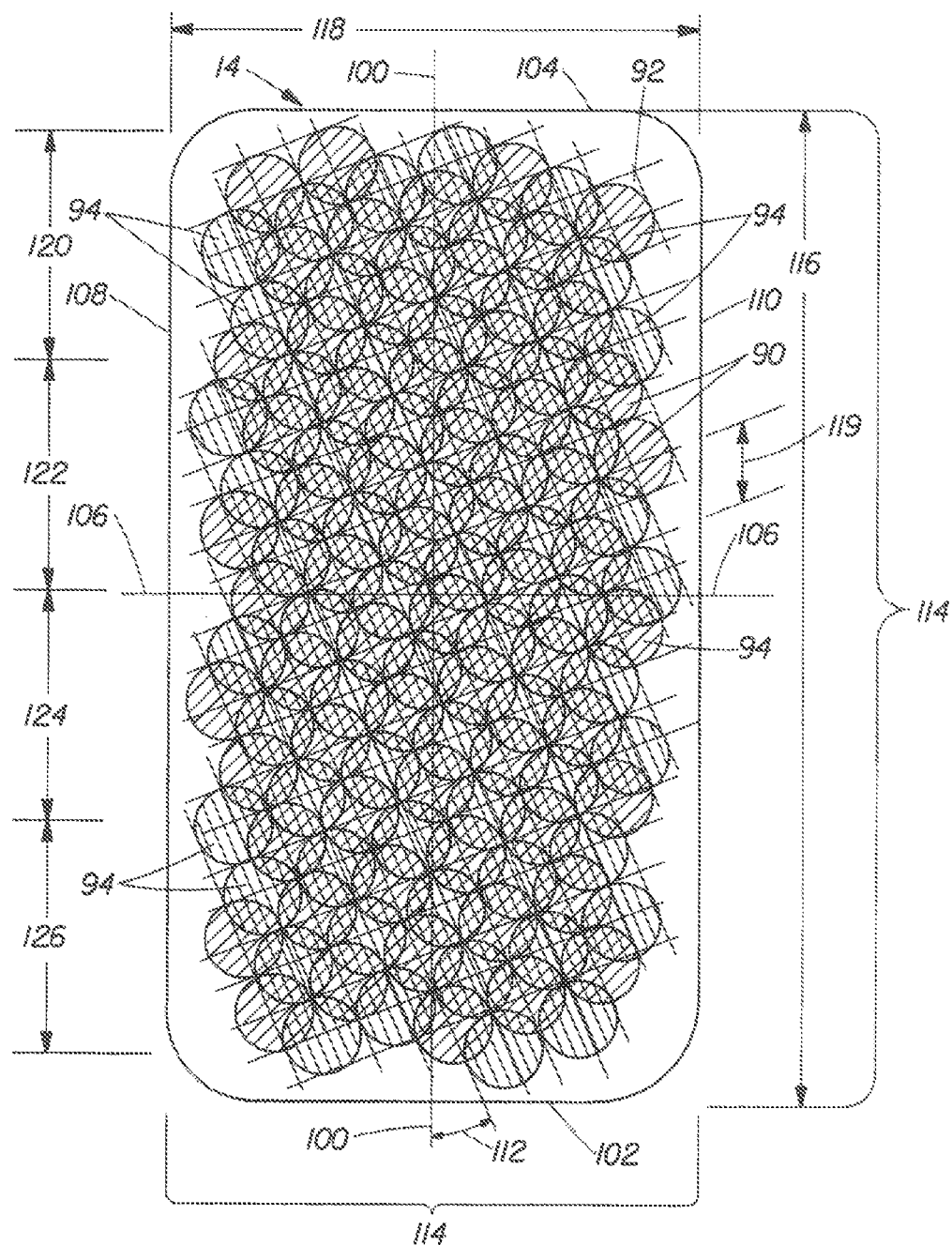
FIG. 8 is a plan view of the absorbent core illustrated in FIGS. 7a and 7b.

"Absorbent particulate polymer material area" as used herein refers to the area of the core wherein the first substrate 64 and second substrate 72 are separated by a multiplicity of superabsorbent particles. In FIG. 8, the boundary of the absorbent particulate polymer material area is defined by the perimeter of the overlapping circles. There may be some extraneous superabsorbent particles outside of this perimeter between the first substrate 64 and second substrate 72.

"Airfelt" is used herein to refer to comminuted wood pulp, which is a form of cellulosic fiber.

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" is used herein to limit the scope of subject matter, such as that in a claim, to the specified materials or steps and those that do not materially affect the basic and novel characteristics of the subject matter.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Fiber" and "filament" are used interchangeably.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson et al. on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

"Substantially cellulose free" is used herein to describe an article, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core.

"Substantially continuously distributed" as used herein indicates that within the absorbent particulate polymer material area, the first substrate 64 and second substrate 72 are separated by a multiplicity of superabsorbent particles. It is recognized that there may be minor incidental contact areas between the first substrate 64 and second substrate 72 within the absorbent particulate polymer material area. Incidental contact areas between the first substrate 64 and second substrate 72 may be intentional or unintentional (e.g. manufacturing artifacts) but do not form geometries such as pillows, pockets, tubes, quilted patterns and the like.

"Thermoplastic adhesive material" as used herein is understood to comprise a polymer composition from which fibers are formed and applied to the superabsorbent material with the intent to immobilize the superabsorbent material in both the dry and wet state. The thermoplastic adhesive material of the present invention forms a fibrous network over the superabsorbent material.

"Thickness" and "caliper" are used herein interchangeably.

Figure 1:
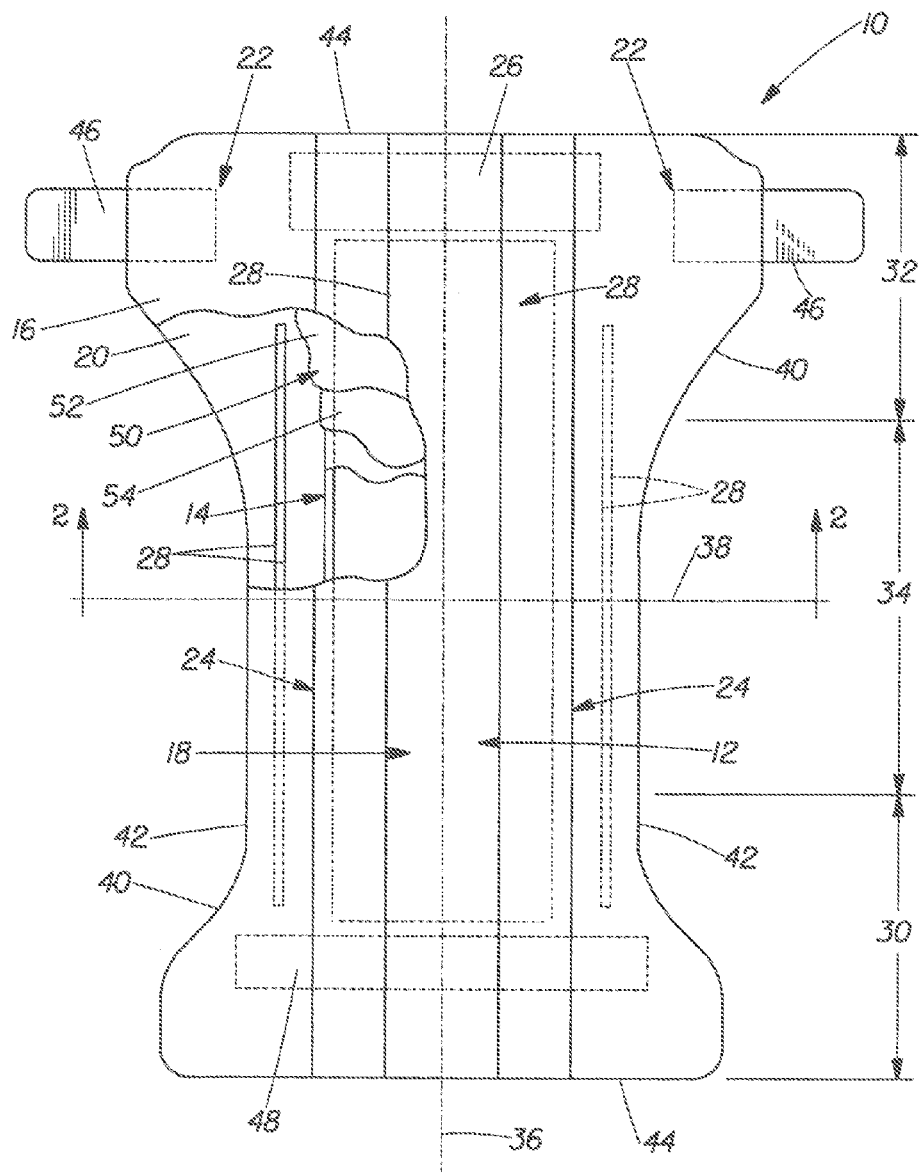
FIG. 1 is a plan view of a diaper in accordance with an embodiment of the present invention.

FIG. 1 is a plan view of a diaper 10 according to a certain embodiment of the present invention. The diaper 10 is shown in its flat out, uncontracted state (i.e., without elastic induced contraction) and portions of the diaper 10 are cut away to more clearly show the underlying structure of the diaper 10. A portion of the diaper 10 that contacts a wearer is facing the viewer in FIG. 1. The diaper 10 generally may comprise a chassis 12 and an absorbent core 14 disposed in the chassis.

The chassis 12 of the diaper 10 in FIG. 1 may comprise the main body of the diaper 10. The chassis 12 may comprise an outer covering 16 including a topsheet 18, which may be liquid pervious, and/or a backsheet 20, which may be liquid impervious. The absorbent core 14 may be encased between the topsheet 18 and the backsheet 20. The chassis 12 may also include side panels 22, elasticized leg cuffs 24, and an elastic waist feature 26.

The leg cuffs 24 and the elastic waist feature 26 may each typically comprise elastic members 28. One end portion of the diaper 10 may be configured as a first waist region 30 of the diaper 10. An opposite end portion of the diaper 10 may be configured as a second waist region 32 of the diaper 10. An intermediate portion of the diaper 10 may be configured as a crotch region 34, which extends longitudinally between the first and second waist regions 30 and 32. The waist regions 30 and 32 may include elastic elements such that they gather about the waist of the wearer to provide improved fit and containment (elastic waist feature 26). The crotch region 34 is that portion of the diaper 10 which, when the diaper 10 is worn, is generally positioned between the wearer's legs.

The diaper 10 is depicted in FIG. 1 with its longitudinal axis 36 and its transverse axis 38. The periphery 40 of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the transverse axis 38 of the diaper 10. The chassis 12 may also comprise a fastening system, which may include at least one fastening member 46 and at least one stored landing zone 48.

The diaper 20 may also include such other features as are known in the art including front and rear ear panels, waist cap features, elastics and the like to provide better fit, containment and aesthetic characteristics. Such additional features are well known in the art and are e.g., described in U.S. Pat. Nos. 3,860,003 and 5,151,092.

In order to keep the diaper 10 in place about the wearer, at least a portion of the first waist region 30 may be attached by the fastening member 46 to at least a portion of the second waist region 32 to form leg opening(s) and an article waist. When fastened, the fastening system carries a tensile load around the article waist. The fastening system may allow an article user to hold one element of the fastening system, such as the fastening member 46, and connect the first waist region 30 to the second waist region 32 in at least two places. This may be achieved through manipulation of bond strengths between the fastening device elements.

According to certain embodiments, the diaper 10 may be provided with a re-closable fastening system or may alternatively be provided in the form of a pant-type diaper. When the absorbent article is a diaper, it may comprise a re-closable fastening system joined to the chassis for securing the diaper to a wearer. When the absorbent article is a pant-type diaper, the article may comprise at least two side panels joined to the chassis and to each other to form a pant. The fastening system and any component thereof may include any material suitable for such a use, including but not limited to plastics, films, foams, nonwoven, woven, paper, laminates, fiber reinforced plastics and the like, or combinations thereof. In certain embodiments, the materials making up the fastening device may be flexible. The flexibility may allow the fastening system to conform to the shape of the body and thus, reduce the likelihood that the fastening system will irritate or injure the wearer's skin.

For unitary absorbent articles, the chassis 12 and absorbent core 14 may form the main structure of the diaper 10 with other features added to form the composite diaper structure. While the topsheet 18, the backsheet 20, and the absorbent core 14 may be assembled in a variety of well-known configurations, preferred diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The topsheet 18 in FIG. 1 may be fully or partially elasticized or may be foreshortened to provide a void space between the topsheet 18 and the absorbent core 14. Exemplary structures including elasticized or foreshortened topsheets are described in more detail in U.S. Pat. No. 5,037,416 entitled "Disposable Absorbent Article Having Elastically Extensible Topsheet" issued to Allen et al. on Aug. 6, 1991; and U.S. Pat. No. 5,269,775 entitled "Trisection Topsheets for Disposable Absorbent Articles and Disposable Absorbent Articles Having Such Trisection Topsheets" issued to Freeland et al. on Dec. 14, 1993.

The backsheet 26 may be joined with the topsheet 18. The backsheet 20 may prevent the exudates absorbed by the absorbent core 14 and contained within the diaper 10 from soiling other external articles that may contact the diaper 10, such as bed sheets and undergarments. In certain embodiments, the backsheet 26 may be substantially impervious to liquids (e.g., urine) and comprise a laminate of a nonwoven and a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 10 while still preventing liquid exudates from passing through the backsheet 10. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E.I. DuPont. Other breathable backsheets including nonwoven webs and apertured formed films are described in U.S. Pat. No. 5,571,096 issued to Dobrin et al. on Nov. 5, 1996.

In certain embodiments, the backsheet of the present invention may have a water vapor transmission rate (WVTR) of greater than about 2000 g/24 h/m$^2$, greater than about 3000 g/24 h/m$^2$, greater than about 5000 g/24 h/m$^2$, greater than about 6000 g/24 h/m$^2$, greater than about 7000 g24 h/m$^2$, greater than about 8000 g/24 h/m$^2$, greater than about 9000 g/24 h/m$^2$, greater than about 10000 g/24 h/m$^2$, greater than about 11000 g/24 h/m$^2$, greater than about 12000 g/24 h/m$^2$, greater than about 15000 g/24 h/m$^2$, measured according to WSP 70.5 (08) at 37.8° C. and 60% Relative Humidity.

Figure 2:
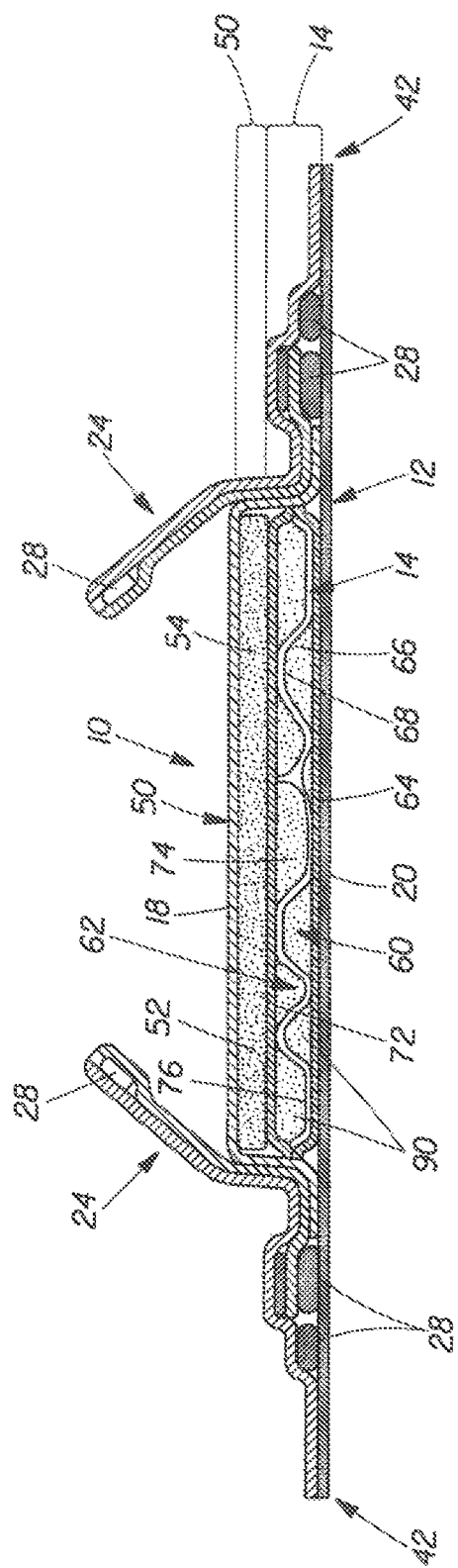
FIG. 2 is a cross sectional view of the diaper shown in FIG. 1 taken along the sectional line 2-2 of FIG. 1.

FIG. 2 shows a cross section of FIG. 1 taken along the sectional line 2-2 of FIG. 1. Starting from the wearer facing side, the diaper 10 may comprise the topsheet 18, the components of the absorbent core 14, and the backsheet 20. According to a certain embodiment, diaper 10 may also comprise an acquisition system 50 disposed between the liquid permeable topsheet 18 and a wearer facing side of the absorbent core 14. The acquisition system 50 may be in direct contact with the absorbent core. The acquisition system 50 may comprise a single layer or multiple layers, such as an upper acquisition layer 52 facing towards the wearer's skin and a lower acquisition 54 layer facing the garment of the wearer. According to a certain embodiment, the acquisition system 50 may function to receive a surge of liquid, such as a gush of urine. In other words, the acquisition system 50 may serve as a temporary reservoir for liquid until the absorbent core 14 can absorb the liquid.

In a certain embodiment, the acquisition system 50 may comprise chemically cross-linked cellulosic fibers. Such cross-linked cellulosic fibers may have desirable absorbency properties. Exemplary chemically cross-linked cellulosic fibers are disclosed in U.S. Pat. No. 5,137,537. In certain embodiments, the chemically cross-linked cellulosic fibers are cross-linked with between about 0.5 mole % and about 10.0 mole % of a $C_2$ to $C_9$ polycarboxylic cross-linking agent or between about 1.5 mole % and about 6.0 mole % of a $C_2$ to $C_9$ polycarboxylic cross-linking agent based on glucose unit. Citric acid is an exemplary cross-linking agent. In other embodiments, polyacrylic acids may be used. Further, according to certain embodiments, the cross-linked cellulosic fibers have a water retention value of about 25 to about 60, or about 28 to about 50, or about 30 to about 45. A method for determining water retention value is disclosed in U.S. Pat. No. 5,137,537. According to certain embodiments, the cross-linked cellulosic fibers may be crimped, twisted, or curled, or a combination thereof including crimped, twisted, and curled.

In a certain embodiment, one or both of the upper and lower acquisition layers 52 and 54 may comprise a non-woven, which may be hydrophilic. Further, according to a certain embodiment, one or both of the upper and lower acquisition layers 52 and 54 may comprise the chemically cross-linked cellulosic fibers, which may or may not form part of a nonwoven material. According to an exemplary embodiment, the upper acquisition layer 52 may comprise a nonwoven, without the cross-linked cellulosic fibers, and the lower acquisition layer 54 may comprise the chemically cross-linked cellulosic fibers. Further, according to an embodiment, the lower acquisition layer 54 may comprise the chemically cross-linked cellulosic fibers mixed with other fibers such as natural or synthetic polymeric fibers. According to exemplary embodiments, such other natural or synthetic polymeric fibers may include high surface area fibers, thermoplastic binding fibers, polyethylene fibers, polypropylene fibers, PET fibers, rayon fibers, lyocell fibers, and mixtures thereof. According to a particular embodiment, the lower acquisition layer 54 has a total dry weight, the cross-linked cellulosic fibers are present on a dry weight basis in the upper acquisition layer in an amount from about 30% to about 95% by weight of the lower acquisition layer 54, and the other natural or synthetic polymeric fibers are present on a dry weight basis in the lower acquisition layer 54 in an amount from about 70% to about 5% by weight of the lower acquisition layer 54. According to another embodiment, the cross-linked cellulosic fibers are present on a dry weight basis in the first acquisition layer in an amount from about 80% to about 90% by weight of the lower acquisition layer 54, and the other natural or synthetic polymeric fibers are present on a dry weight basis in the lower acquisition layer 54 in an amount from about 20% to about 10% by weight of the lower acquisition layer 54.

According to a certain embodiment, the lower acquisition layer 54 desirably has a high fluid uptake capability. Fluid uptake is measured in grams of absorbed fluid per gram of absorbent material and is expressed by the value of "maximum uptake." A high fluid uptake corresponds therefore to a high capacity of the material and is beneficial, because it ensures the complete acquisition of fluids to be absorbed by an acquisition material. According to exemplary embodiments, the lower acquisition layer 54 has a maximum uptake of about 10 g/g.

A relevant attribute of the upper acquisition layer 54 is its Median Desorption Pressure, MDP. The MDP is a measure of the capillary pressure that is required to dewater the lower acquisition layer 54 to about 50% of its capacity at 0 cm capillary suction height under an applied mechanical pressure of 0.3 psi. Generally, a relatively lower MDP may be useful. The lower MDP may allow the lower acquisition layer 54 to more efficiently drain the upper acquisition material. Without wishing to be bound by theory, a given distribution material may have a definable capillary suction. The ability of the lower acquisition layer 54 to move liquid vertically via capillary forces will be directly impacted by gravity and the opposing capillary forces associated with desorption of the upper acquisition layer. Minimizing these capillary forces may positively impact the performance of the lower acquisition layer 54. However, in a certain embodiment the lower acquisition layer 54 may also have adequate capillary absorption suction in order to drain the layers above (upper acquisition layer 52 and topsheet 18, in particular) and to temporarily hold liquid until the liquid can be partitioned away by the absorbent core components. Therefore, in a certain embodiment, the lower acquisition layer 54 may have a minimum MDP of greater than 5 cm. Further, according to exemplary embodiments, the lower acquisition layer 54 has an MDP value of less than about 20.5 cm $H_2O$, or less than about 19 cm $H_2O$, or less than about 18 cm $H_2O$ to provide for fast acquisition.

The methods for determining MDP and maximum uptake are disclosed in U.S. patent application Ser. No. 11/600,691 (Flohr et al.). For example, according to a first embodiment, the lower acquisition layer 54 may comprise about 70% by weight of chemically cross-linked cellulose fibers, about 10% by weight polyester (PET), and about 20% by weight untreated pulp fibers. According to a second embodiment, the lower acquisition layer 54 may comprise about 70% by weight chemically cross-linked cellulose fibers, about 20% by weight lyocell fibers, and about 10% by weight PET fibers. According to a third embodiment, the lower acquisition layer 54 may comprise about 68% by weight chemically cross-linked cellulose fibers, about 16% by weight untreated pulp fibers, and about 16% by weight PET fibers. In one embodiment, the lower acquisition layer 54 may comprise from about 90-100% by weight chemically cross-linked cellulose fibers.

Suitable non-woven materials for the upper and lower acquisition layers 52 and 54 include, but are not limited to SMS material, comprising a spunbonded, a melt-blown and a further spunbonded layer. In certain embodiments, permanently hydrophilic non-wovens, and in particular, nonwovens with durably hydrophilic coatings are desirable. Another suitable embodiment comprises a SMMS-structure. In certain embodiments, the non-wovens are porous.

In certain embodiments, suitable non-woven materials may include, but are not limited to synthetic fibers, such as PE, PET, and PP. As polymers used for nonwoven production may be inherently hydrophobic, they may be coated with hydrophilic coatings. One way to produce nonwovens with durably hydrophilic coatings, is via applying a hydrophilic monomer and a radical polymerization initiator onto the nonwoven, and conducting a polymerization activated via UV light resulting in monomer chemically bound to the surface of the nonwoven as described in co-pending U.S. Patent Publication No. 2005/0159720. Another way to produce nonwovens with durably hydrophilic coatings is to coat the nonwoven with hydrophilic nanoparticles as described in co-pending applications U.S. Pat. No. 7,112,621 to Rohrbaugh et al. and in PCT Application Publication WO 02/064877.

Typically, nanoparticles have a largest dimension of below 750 nm. Nanoparticles with sizes ranging from 2 to 750 nm may be economically produced. An advantage of nanoparticles is that many of them can be easily dispersed in water solution to enable coating application onto the nonwoven, they typically form transparent coatings, and the coatings applied from water solutions are typically sufficiently durable to exposure to water. Nanoparticles can be organic or inorganic, synthetic or natural. Inorganic nanoparticles generally exist as oxides, silicates, and/or, carbonates. Typical examples of suitable nanoparticles are layered clay minerals (e.g., LAPONITE™ from Southern Clay Products, Inc. (USA), and Boehmite alumina (e.g., Disperal P2™ from North American Sasol. Inc.). According to a certain embodiment, a suitable nanoparticle coated non-woven is that disclosed in the co-pending patent application Ser. No. 10/758,066 entitled "Disposable absorbent article comprising a durable hydrophilic core wrap" to Ekaterina Anatolyevna Ponomarenko and Mattias NMN Schmidt.

Further useful non-wovens are described in U.S. Pat. No. 6,645,569 to Cramer et al., U.S. Pat. No. 6,863,933 to Cramer et al., U.S. Pat. No. 7,112,621 to Rohrbaugh et al., and co-pending patent application Ser. No. 10/338,603 to Cramer et al. and Ser. No. 10/338,610 to Cramer et al.

In some cases, the nonwoven surface can be pre-treated with high energy treatment (corona, plasma) prior to application of nanoparticle coatings. High energy pre-treatment typically temporarily increases the surface energy of a low surface energy surface (such as PP) and thus enables better wetting of a nonwoven by the nanoparticle dispersion in water.

Notably, permanently hydrophilic non-wovens are also useful in other parts of an absorbent article. For example, topsheets and absorbent core layers comprising permanently hydrophilic non-wovens as described above have been found to work well.

According to a certain embodiment, the upper acquisition layer 52 may comprise a material that provides good recovery when external pressure is applied and removed. Further, according to a certain embodiment, the upper acquisition layer 52 may comprise a blend of different fibers selected, for example from the types of polymeric fibers described above. In some embodiments, at least a portion of the fibers may exhibit a spiral-crimp which has a helical shape. In some embodiments, the upper acquisition layer 52 may comprise fibers having different degrees or types of crimping, or both. For example, one embodiment may include a mixture of fibers having about 8 to about 12 crimps per inch (cpi) or about 9 to about 10 cpi, and other fibers having about 4 to about 8 cpi or about 5 to about 7 cpi. Different types of crimps include, but are not limited to a 2D crimp or "flat crimp" and a 3D or spiral-crimp. According to a certain embodiment, the fibers may include bi-component fibers, which are individual fibers each comprising different materials, usually a first and a second polymeric material. It is believed that the use of side-by-side bi-component fibers is beneficial for imparting a spiral-crimp to the fibers.

The upper acquisition layer 52 may be stabilized by a latex binder, for example a styrene-butadiene latex binder (SB latex), in a certain embodiment. Processes for obtaining such lattices are known, for example, from EP 149 880 (Kwok) and US 2003/0105190 (Diehl et al.). In certain embodiments, the binder may be present in the upper acquisition layer 52 in excess of about 12%, about 14% or about 16% by weight. For certain embodiments, SB latex is available under the trade name GENFLO™ 3160 (OMNOVA Solutions Inc.; Akron, Ohio).

Figure 3:
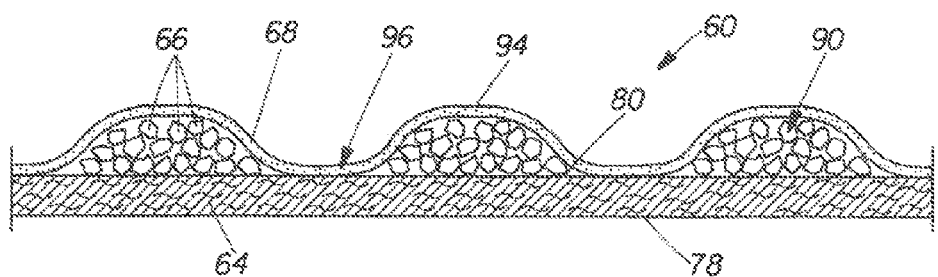
FIG. 3 is a partial cross sectional view of an absorbent core layer in accordance with an embodiment of this invention.

The absorbent core 14 in FIGS. 1-8 generally is disposed between the topsheet 18 and the backsheet 20 and comprises two layers, a first absorbent layer 60 and a second absorbent layer 62. As best shown in FIG. 3, the first absorbent layer 60 of the absorbent core 14 comprises a substrate 64, an absorbent particular polymer material 66 on the substrate 64, and a thermoplastic composition 68 on the absorbent particulate polymer material 66 and at least portions of the first substrate 64 as an adhesive for covering and immobilizing the absorbent particulate polymer material 66 on the first substrate 64. According to another embodiment illustrated in FIG. 4, the first absorbent layer 60 of the absorbent core 14 may also include a cover layer 70 on the thermoplastic composition 68.

Likewise, as best illustrated in FIG. 2, the second absorbent layer 62 of the absorbent core 14 may also include a substrate 72, an absorbent particulate polymer material 74 on the second substrate 72, and a thermoplastic composition 66 on the absorbent particulate polymer material 74 and at least a portion of the second substrate 72 for immobilizing the absorbent particulate polymer material 74 on the second substrate 72.

Figure 4:
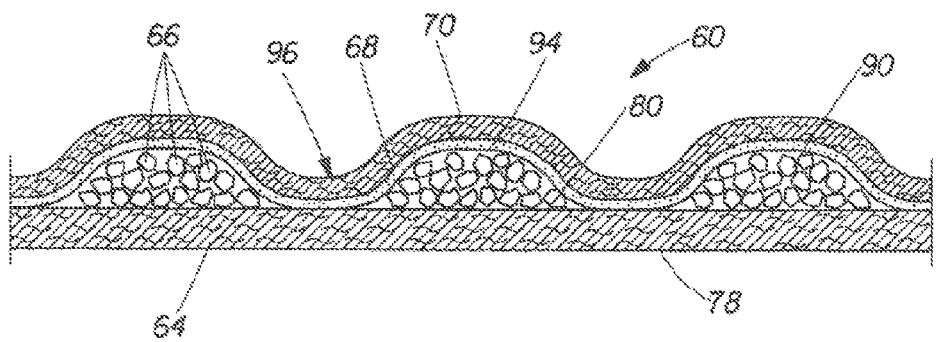
FIG. 4 is a partial cross sectional view of an absorbent core layer in accordance with another embodiment of this invention.

Although not illustrated, the second absorbent layer 62 may also include a cover layer such as the cover layer 70 illustrated in FIG. 4.

The substrate 64 of the first absorbent layer 60 may be referred to as a dusting layer and has a first surface 78 which faces the backsheet 20 of the diaper 10 and a second surface 80 which faces the absorbent particulate polymer material 66. Likewise, the substrate 72 of the second absorbent layer 62 may be referred to as a core cover and has a first surface 82 facing the topsheet 18 of the diaper 10 and a second surface 84 facing the absorbent particulate polymer material 74. The first and second substrates 64 and 72 may be adhered to one another with adhesive about the periphery to form an envelope about the absorbent particulate polymer materials 66 and 74 to hold the absorbent particulate polymer material 66 and 74 within the absorbent core 14.

According to a certain embodiment, the substrates 64 and 72 of the first and second absorbent layers 60 and 62 may be a non-woven material, such as those nonwoven materials described above. In certain embodiments, the non-wovens are porous and in one embodiment has a pore size of about 32 microns.

As illustrated in FIGS. 1-8, the absorbent particulate polymer material 66 and 74 is deposited on the respective substrates 64 and 72 of the first and second absorbent layers 60 and 62 in clusters 90 of particles to form a grid pattern 92 comprising land areas 94 and junction areas 96 between the land areas 94. As defined herein, land areas 94 are areas where the thermoplastic adhesive material does not contact the nonwoven substrate or the auxiliary adhesive directly; junction areas 96 are areas where the thermoplastic adhesive material does contact the nonwoven substrate or the auxiliary adhesive directly. The junction areas 96 in the grid pattern 92 contain little or no absorbent particulate polymer material 66 and 74. The land areas 94 and junction areas 96 can have a variety of shapes including, but not limited to, circular, oval, square, rectangular, triangular, and the like.

The grid pattern shown in FIG. 8 is a square grid with regular spacing and size of the land areas. Other grid patterns including hexagonal, rhombic, orthorhombic, parallelogram, triangular, rectangular, and combinations thereof may also be used. The spacing between the grid lines may be regular or irregular.

The size of the land areas 94 in the grid patterns 92 may vary. According to certain embodiments, the width 119 of the land areas 94 in the grid patterns 92 ranges from about 8 mm to about 12 mm. In a certain embodiment, the width of the land areas 94 is about 10 mm. The junction areas 96, on the other hand, in certain embodiments, have a width or larger span of less than about 5 mm, less than about 3 mm, less than about 2 mm, less than about 1.5 mm, less than about 1 mm, or less than about 0.5 mm.

As shown in FIG. 8, the absorbent core 14 has a longitudinal axis 100 extending from a rear end 102 to a front end 104 and a transverse axis 106 perpendicular to the longitudinal axis 100 extending from a first edge 108 to a second edge 110. The grid pattern 92 of absorbent particulate polymer material clusters 90 is arranged on the substrates 64 and 72 of the respective absorbent layers 60 and 62 such that the grid pattern 92 formed by the arrangement of land areas 94 and junction areas 96 forms a pattern angle 112. The pattern angle 112 may be 0, greater than 0, or 15 to 30 degrees, or from about 5 to about 85 degrees, or from about 10 to about 60 degrees, or from about 15 to about 30 degrees.

Figure 7A:
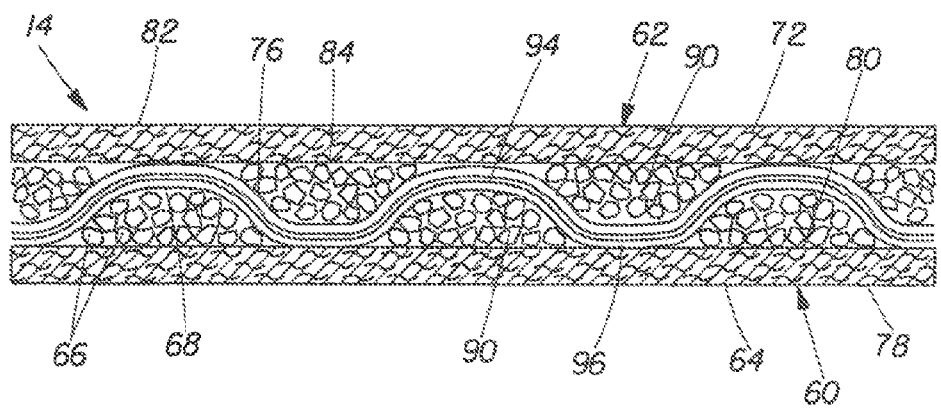
FIG. 7a is a partial sectional view of an absorbent core comprising a combination of the first and second absorbent core layers illustrated in FIGS. 5 and 6.
Figure 7B:
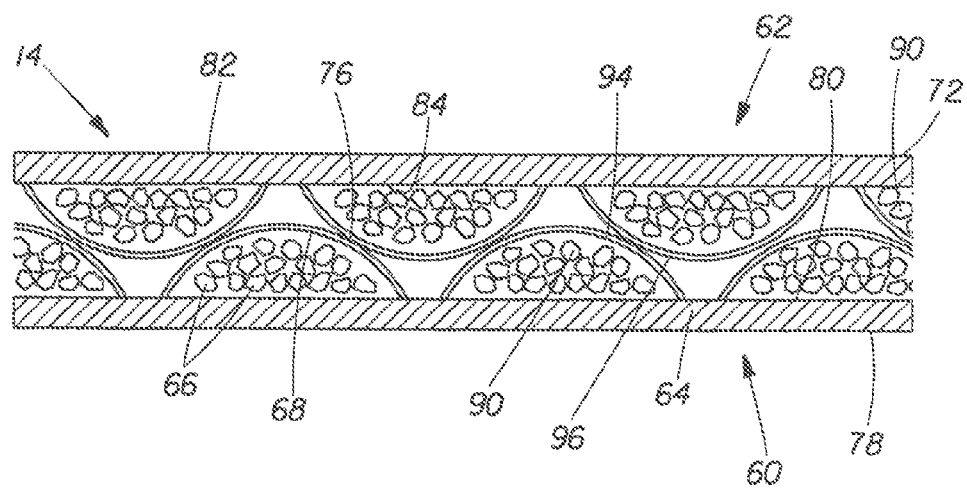
FIG. 7b is a partial sectional view of an absorbent core comprising a combination of the first and second absorbent core layers illustrated in FIGS. 5 and 6.

As best seen in FIGS. 7a, 7b, and 8, the first and second layers 60 and 62 may be combined to form the absorbent core 14. The absorbent core 14 has an absorbent particulate polymer material area 114 bounded by a pattern length 116 and a pattern width 118. The extent and shape of the absorbent particulate polymer material area 114 may vary depending on the desired application of the absorbent core 14 and the particular absorbent article in which it may be incorporated. In a certain embodiment, however, the absorbent particulate polymer material area 114 extends substantially entirely across the absorbent core 14, such as is illustrated in FIG. 8.

The first and second absorbent layers 60 and 62 may be combined together to form the absorbent core 14 such that the grid patterns 92 of the respective first and second absorbent layers 62 and 64 are offset from one another along the length and/or width of the absorbent core 14. The respective grid patterns 92 may be offset such that the absorbent particulate polymer material 66 and 74 is substantially continuously distributed across the absorbent particulate polymer area 114. In a certain embodiment, absorbent particulate polymer material 66 and 74 is substantially continuously distributed across the absorbent particulate polymer material area 114 despite the individual grid patterns 92 comprising absorbent particulate polymer material 66 and 74 discontinuously distributed across the first and second substrates 64 and 72 in clusters 90. In a certain embodiment, the grid patterns may be offset such that the land areas 94 of the first absorbent layer 60 face the junction areas 96 of the second absorbent layer 62 and the land areas of the second absorbent layer 62 face the junction areas 96 of the first absorbent layer 60. When the land areas 94 and junction areas 96 are appropriately sized and arranged, the resulting combination of absorbent particulate polymer material 66 and 74 is a substantially continuous layer of absorbent particular polymer material across the absorbent particulate polymer material area 114 of the absorbent core 14 (i.e. first and second substrates 64 and 72 do not form a plurality of pockets, each containing a cluster 90 of absorbent particulate polymer material 66 therebetween). In a certain embodiment, respective grid patterns 92 of the first and second absorbent layer 60 and 62 may be substantially the same.

In a certain embodiment as illustrated in FIG. 8, the amount of absorbent particulate polymer material 66 and 74 may vary along the length 116 of the grid pattern 92. In a certain embodiment, the grid pattern may be divided into absorbent zones 120, 122, 124, and 126, in which the amount of absorbent particulate polymer material 66 and 74 varies from zone to zone. As used herein, "absorbent zone" refers to a region of the absorbent particulate polymer material area having boundaries that are perpendicular to the longitudinal axis shown in FIG. 8. The amount of absorbent particulate polymer material 66 and 74 may, in a certain embodiment, gradually transition from one of the plurality of absorbent zones 120, 122, 124, and 126 to another. This gradual transition in amount of absorbent particulate polymer material 66 and 74 may reduce the possibility of cracks forming in the absorbent core 14.

The amount of absorbent particulate polymer material 66 and 74 present in the absorbent core 14 may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In a particular embodiment, the absorbent core 14 consists essentially of the first and second substrates 64 and 72, the absorbent particulate polymer material 66 and 74, and the thermoplastic adhesive composition 68 and 76. In an embodiment, the absorbent core 14 may be substantially cellulose free.

According to certain embodiments, the weight of absorbent particulate polymer material 66 and 74 in at least one freely selected first square measuring 1 cm×1 cm may be at least about 10%, or 20%, or 30%, 40% or 50% higher than the weight of absorbent particulate polymer material 66 and 74 in at least one freely selected second square measuring 1 cm×1 cm. In a certain embodiment, the first and the second square are centered about the longitudinal axis.

The absorbent particulate polymer material area, according to an exemplary embodiment, may have a relatively narrow width in the crotch area of the absorbent article for increased wearing comfort. Hence, the absorbent particulate polymer material area, according to an embodiment, may have a width as measured along a transverse line which is positioned at equal distance to the front edge and the rear edge of the absorbent article, which is less than about 100 mm, 90 mm, 80 mm, 70 mm, 60 mm or even less than about 50 mm.

It has been found that, for most absorbent articles such as diapers, the liquid discharge occurs predominately in the front half of the diaper. The front half of the absorbent core 14 should therefore comprise most of the absorbent capacity of the core. Thus, according to certain embodiments, the front half of said absorbent core 14 may comprise more than about 60% of the superabsorbent material, or more than about 65%, 70%, 75%, 80%, 85%, or 90% of the superabsorbent material.

In certain embodiments, the absorbent core 14 may further comprise any absorbent material that is generally compressible, conformable, non-irritating to the wearer's skin, and capable of absorbing and retaining liquids such as urine and other certain body exudates. In such embodiments, the absorbent core 14 may comprise a wide variety of liquid-absorbent materials commonly used in disposable diapers and other absorbent articles such as comminuted wood pulp, which is generally referred to as airfelt, creped cellulose wadding, melt blown polymers, including co-form, chemically stiffened, modified or cross-linked cellulosic fibers, tissue, including tissue wraps and tissue laminates, absorbent foams, absorbent sponges, or any other known absorbent material or combinations of materials. The absorbent core 14 may further comprise minor amounts (typically less than about 10%) of materials, such as adhesives, waxes, oils and the like.

Exemplary absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,207 (Dyer et al.); U.S. Pat. No. 5,397,316 (LaVon et al.); and U.S. Pat. No. 5,625,222 (DesMarais et al.).

The thermoplastic adhesive material 68 and 76 may serve to cover and at least partially immobilize the absorbent particulate polymer material 66 and 74. In one embodiment of the present invention, the thermoplastic adhesive material 68 and 76 can be disposed essentially uniformly within the absorbent particulate polymer material 66 and 74, between the polymers. However, in a certain embodiment, the thermoplastic adhesive material 68 and 76 may be provided as a fibrous layer which is at least partially in contact with the absorbent particulate polymer material 66 and 74 and partially in contact with the substrate layers 64 and 72 of the first and second absorbent layers 60 and 62. FIGS. 3, 4, and 7 show such a structure, and in that structure, the absorbent particulate polymer material 66 and 74 is provided as a discontinuous layer, and a layer of fibrous thermoplastic adhesive material 68 and 76 is laid down onto the layer of absorbent particulate polymer material 66 and 74, such that the thermoplastic adhesive material 68 and 76 is in direct contact with the absorbent particulate polymer material 66 and 74, but also in direct contact with the second surfaces 80 and 84 of the substrates 64 and 72, where the substrates are not covered by the absorbent particulate polymer material 66 and 74. This imparts an essentially three-dimensional structure to the fibrous layer of thermoplastic adhesive material 68 and 76, which in itself is essentially a two-dimensional structure of relatively small thickness, as compared to the dimension in length and width directions. In other words, the thermoplastic adhesive material 68 and 76 undulates between the absorbent particulate polymer material 68 and 76 and the second surfaces of the substrates 64 and 72.

Thereby, the thermoplastic adhesive material 68 and 76 may provide cavities to cover the absorbent particulate polymer material 66 and 74, and thereby immobilizes this material. In a further aspect, the thermoplastic adhesive material 68 and 76 bonds to the substrates 64 and 72 and thus affixes the absorbent particulate polymer material 66 and 74 to the substrates 64 and 72. Thus, in accordance with certain embodiments, the thermoplastic adhesive material 68 and 76 immobilizes the absorbent particulate polymer material 66 and 74 when wet, such that the absorbent core 14 achieves an absorbent particulate polymer material loss of no more than about 70%, 60%, 50%, 40%, 30%, 20%, 10% according to the Wet Immobilization Test described herein. Some thermoplastic adhesive materials will also penetrate into both the absorbent particulate polymer material 66 and 74 and the substrates 64 and 72, thus providing for further immobilization and affixation. Of course, while the thermoplastic adhesive materials disclosed herein provide a much improved wet immobilization (i.e., immobilization of absorbent material when the article is wet or at least partially loaded), these thermoplastic adhesive materials may also provide a very good immobilization of absorbent material when the absorbent core 14 is dry. The thermoplastic adhesive material 68 and 76 may also be referred to as a hot melt adhesive.

Without wishing to be bound by theory, it has been found that those thermoplastic adhesive materials which are most useful for immobilizing the absorbent particulate polymer material 66 and 74 combine good cohesion and good adhesion behavior. Good adhesion may promote good contact between the thermoplastic adhesive material 68 and 76 and the absorbent particulate polymer material 66 and 74 and the substrates 64 and 72. Good cohesion reduces the likelihood that the adhesive breaks, in particular in response to external forces, and namely in response to strain. When the absorbent core 14 absorbs liquid, the absorbent particulate polymer material 66 and 74 swells and subjects the thermoplastic adhesive material 68 and 76 to external forces. In certain embodiments, the thermoplastic adhesive material 68 and 76 may allow for such swelling, without breaking and without imparting too many compressive forces, which would restrain the absorbent particulate polymer material 66 and 74 from swelling.

In accordance with certain embodiments, the thermoplastic adhesive material 68 and 76 may comprise, in its entirety, a single thermoplastic polymer or a blend of thermoplastic polymers, having a softening point, as determined by the ASTM Method D-36-95 "Ring and Ball", in the range between 50° C. and 300° C., or alternatively the thermoplastic adhesive material may be a hot melt adhesive comprising at least one thermoplastic polymer in combination with other thermoplastic diluents such as tackifying resins, plasticizers and additives such as antioxidants. In certain embodiments, the thermoplastic polymer has typically a molecular weight (Mw) of more than 10,000 and a glass transition temperature (Tg) usually below room temperature or $-6° C. > Tg < 16° C.$ In certain embodiments, typical concentrations of the polymer in a hot melt are in the range of about 20 to about 40% by weight. In certain embodiments, thermoplastic polymers may be water insensitive. Exemplary polymers are (styrenic) block copolymers including A-B-A triblock structures, A-B diblock structures and $(A-B)_n$ radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof.

Other suitable thermoplastic polymers that may be employed are metallocene polyolefins, which are ethylene polymers prepared using single-site or metallocene catalysts. Therein, at least one comonomer can be polymerized with ethylene to make a copolymer, terpolymer or higher order polymer. Also applicable are amorphous polyolefins or amorphous polyalphaolefins (APAO) which are homopolymers, copolymers or terpolymers of C2 to C8 alpha olefins.

In exemplary embodiments, the tackifying resin has typically a Mw below 5,000 and a Tg usually above room temperature, typical concentrations of the resin in a hot melt are in the range of about 30 to about 60%, and the plasticizer has a low Mw of typically less than 1,000 and a Tg below room temperature, with a typical concentration of about 0 to about 15%.

In certain embodiments, the thermoplastic adhesive material 68 and 76 is present in the form of fibers. In some embodiments, the fibers will have an average thickness of about 1 to about 50 micrometers or about 1 to about 35 micrometers and an average length of about 5 mm to about 50 mm or about 5 mm to about 30 mm. To improve the adhesion of the thermoplastic adhesive material 68 and 76 to the substrates 64 and 72 or to any other layer, in particular any other non-woven layer, such layers may be pre-treated with an auxiliary adhesive.

In certain embodiments, the thermoplastic adhesive material 68 and 76 will meet at least one, or several, or all of the following parameters:

An exemplary thermoplastic adhesive material 68 and 76 may have a storage modulus G' measured at 20° C. of at least 30,000 Pa and less than 300,000 Pa, or less than 200,000 Pa, or between 140,000 Pa and 200,000 Pa, or less than 100,000 Pa. In a further aspect, the storage modulus G' measured at 35° C. may be greater than 80,000 Pa. In a further aspect, the storage modulus G' measured at 60° C. may be less than 300,000 Pa and more than 18,000 Pa, or more than 24,000 Pa, or more than 30,000 Pa, or more than 90,000 Pa. In a further aspect, the storage modulus G' measured at 90° C. may be less than 200,000 Pa and more than 10,000 Pa, or more than 20,000 Pa, or more then 30,000 Pa. The storage modulus measured at 60° C. and 90° C. may be a measure for the form stability of the thermoplastic adhesive material at elevated ambient temperatures. This value is particularly important if the absorbent product is used in a hot climate where the thermoplastic adhesive material would lose its integrity if the storage modulus G' at 60° C. and 90° C. is not sufficiently high.

Figure 9:
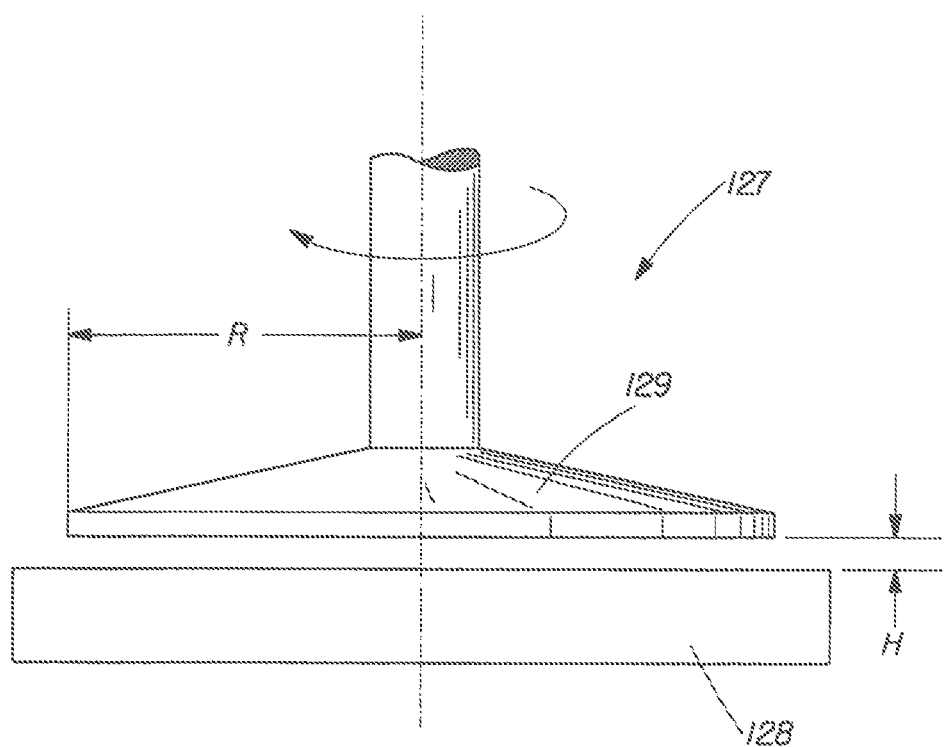
FIG. 9 is a schematic representation of a rheometer.

G' is measured using a rheometer as schematically shown in FIG. 9 for the purpose of general illustration only. The rheometer 127 is capable of applying a shear stress to the adhesive and measuring the resulting strain (shear deformation) response at constant temperature. The adhesive is placed between a Peltier-element acting as lower, fixed plate 128 and an upper plate 129 with a radius R of e.g., 10 mm, which is connected to the drive shaft of a motor to generate the shear stress. The gap between both plates has a height H of e.g., 1500 micron. The Peltier-element enables temperature control of the material (+0.5° C.). The strain rate and frequency should be chosen such that all measurements are made in the linear viscoelastic region.

The absorbent core 14 may also comprise an auxiliary adhesive which is not illustrated in the figures. The auxiliary adhesive may be deposited on the first and second substrates 64 and 72 of the respective first and second absorbent layers 60 and 62 before application of the absorbent particulate polymer material 66 and 74 for enhancing adhesion of the absorbent particulate polymer materials 66 and 74 and the thermoplastic adhesive material 68 and 76 to the respective substrates 64 and 72. The auxiliary glue may also aid in immobilizing the absorbent particulate polymer material 66 and 74 and may comprise the same thermoplastic adhesive material as described hereinabove or may also comprise other adhesives including but not limited to sprayable hot melt adhesives, such as H.B. Fuller Co. (St. Paul, Minn.) Product No. HL-1620-B. The auxiliary glue may be applied to the substrates 64 and 72 by any suitable means, but according to certain embodiments, may be applied in about 0.5 to about 1 mm wide slots spaced about 0.5 to about 2 mm apart.

The cover layer 70 shown in FIG. 4 may comprise the same material as the substrates 64 and 72, or may comprise a different material. In certain embodiments, suitable materials for the cover layer 70 are the non-woven materials, typically the materials described above as useful for the substrates 64 and 72.

Figure 10:
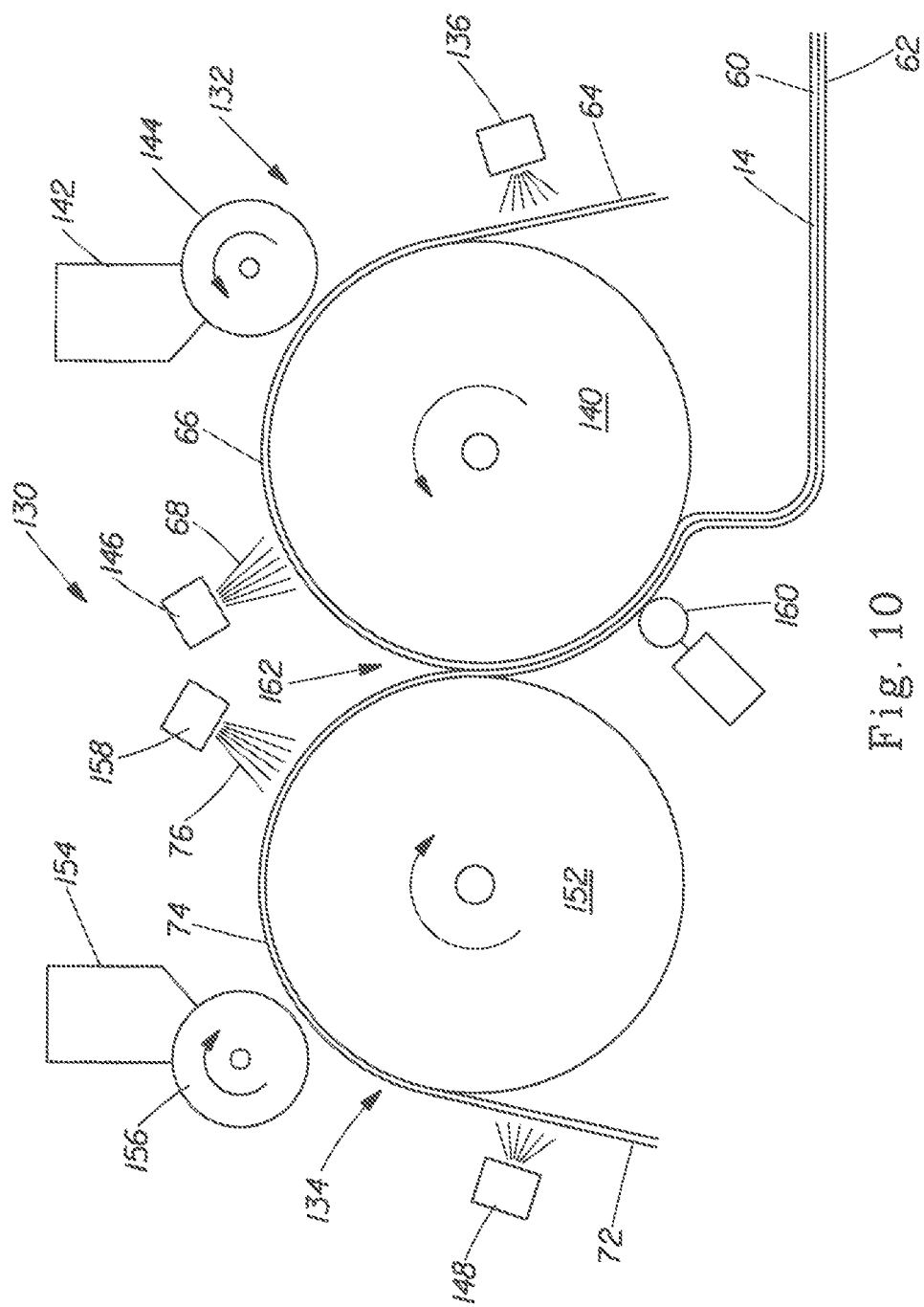
FIG. 10 is a schematic illustration of a process for making an absorbent core in accordance with an embodiment of this invention.

A printing system 130 for making an absorbent core 14 in accordance with an embodiment of this invention is illustrated in FIG. 10 and may generally comprise a first printing unit 132 for forming the first absorbent layer 60 of the absorbent core 14 and a second printing unit 134 for forming the second absorbent layer 62 of the absorbent core 14.

The first printing unit 132 may comprise a first auxiliary adhesive applicator 136 for applying an auxiliary adhesive to the substrate 64, which may be a nonwoven web, a first rotatable support roll 140 for receiving the substrate 64, a hopper 142 for holding absorbent particulate polymer material 66, a printing roll 144 for transferring the absorbent particulate polymer material 66 to the substrate 64, and a thermoplastic adhesive material applicator 146 for applying the thermoplastic adhesive material 68 to the substrate 64 and the absorbent particulate polymer 66 material thereon.

The second printing unit 134 may comprise a second auxiliary adhesive applicator 148 for applying an auxiliary adhesive to the second substrate 72, a second rotatable support roll 152 for receiving the second substrate 72, a second hopper 154 for holding the absorbent particulate polymer material 74, a second printing roll 156 for transferring the absorbent particulate polymer material 74 from the hopper 154 to the second substrate 72, and a second thermoplastic adhesive material applicator 158 for applying the thermoplastic adhesive material 76 to the second substrate 72 and the absorbent particulate polymer material 74 thereon.

The printing system 130 also includes a guide roller 160 for guiding the formed absorbent core from a nip 162 between the first and second rotatable support rolls 140 and 152.

The first and second auxiliary applicators 136 and 148 and the first and second thermoplastic adhesive material applicators 146 and 158 may be a nozzle system which can provide a relatively thin but wide curtain of thermoplastic adhesive material.

Figure 11:
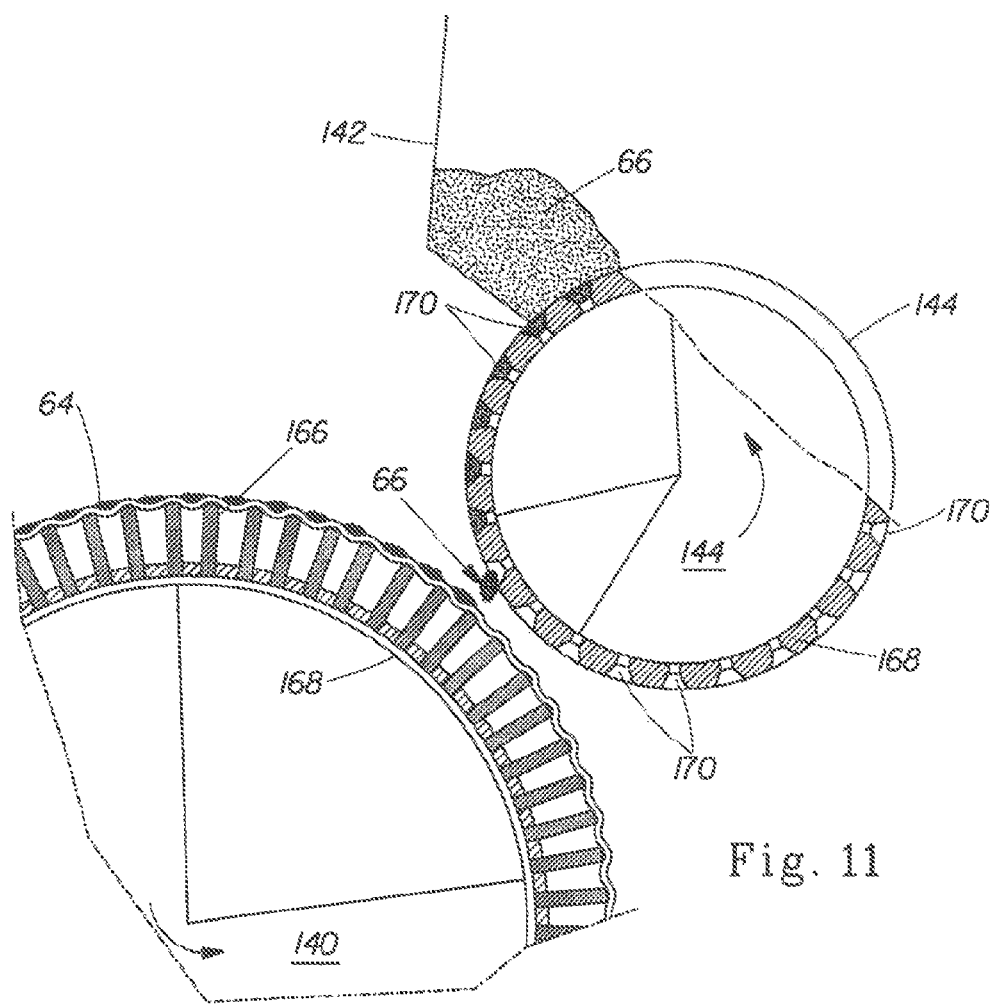
FIG. 11 is a partial sectional view of an apparatus for making an absorbent core in accordance with an embodiment of this invention.
Figure 14:
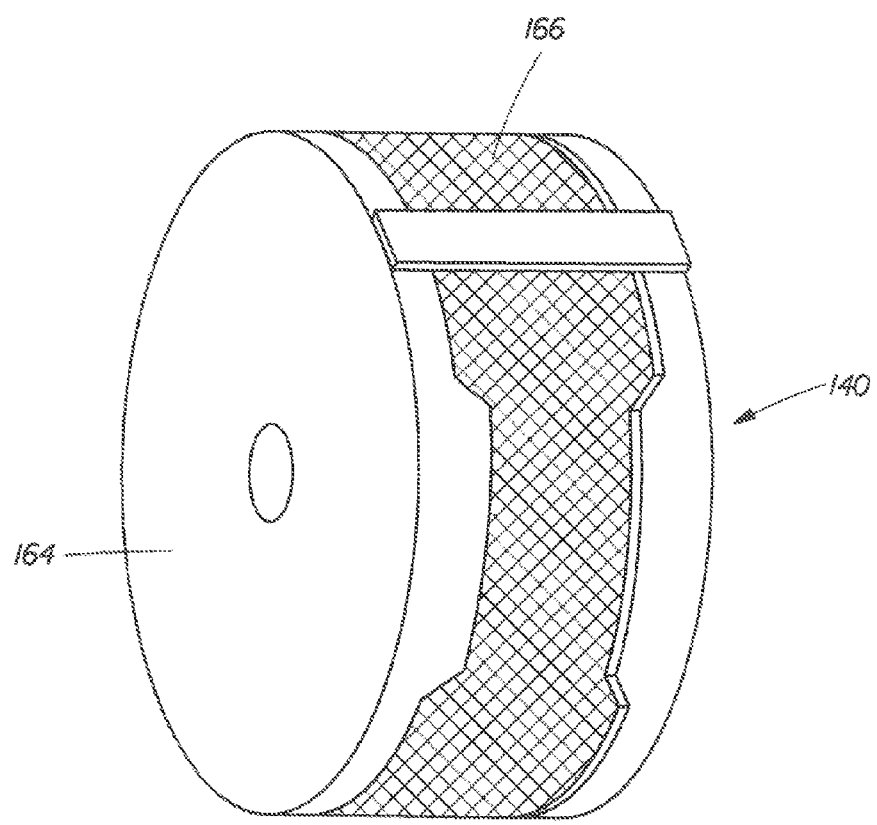
FIG. 14 is a perspective view of the supporting roll illustrated in FIG. 12.

Turning to FIG. 11, portions of the first hopper 142, first support roll 140, and first printing roll 144 are illustrated. As also shown in FIG. 14, the first rotatable support roll 140, which has the same structure as the second rotatable support roll 152, comprises a rotatable drum 164 and a peripheral vented support grid 166 for receiving the first substrate 64.

Figure 12:
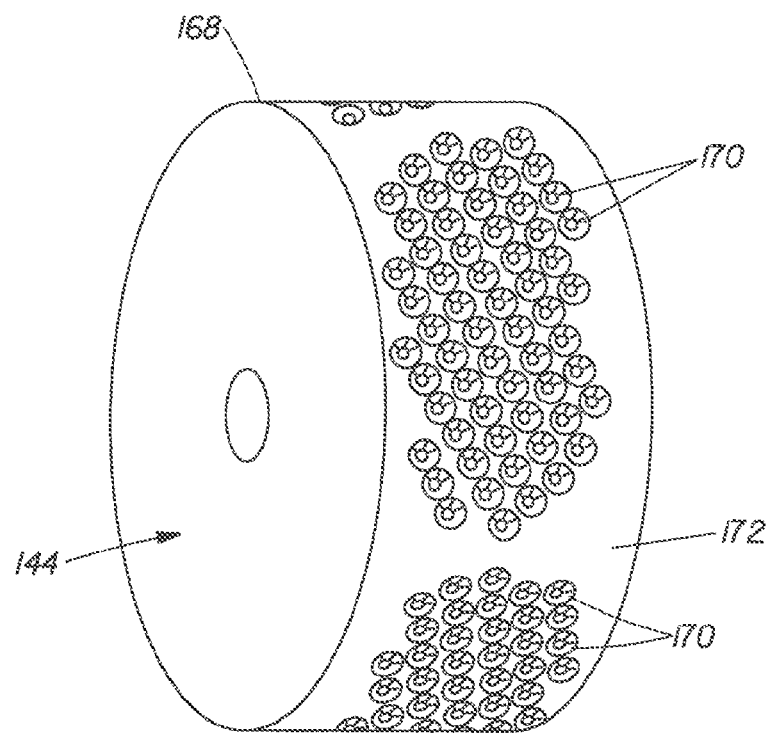
FIG. 12 is a perspective view of the printing roll illustrated in FIG. 11.
Figure 13:
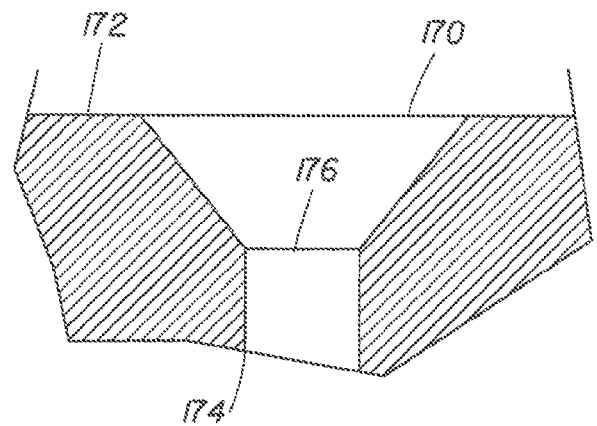
FIG. 13 is a partial sectional view of the printing roll illustrated in FIG. 12 showing an absorbent particulate polymer material reservoir.

As also illustrated in FIG. 12, the first printing roll 144, which has the same structure as the second printing roll 156, comprises a rotatable drum 168 and a plurality of absorbent particulate polymer material reservoirs 170 in a peripheral surface 172 of the drum 168. The reservoirs 170 best illustrated in FIG. 13, may have a variety of shapes, including cylindrical, conical, or any other shape. The reservoirs 170 may lead to an air passage 174 in the drum 168 and comprise a vented cover 176 for holding adhesive particulate polymer material 66 in the reservoir and preventing the adhesive particulate polymer material 66 from falling or being pulled into the air passage 174.

Figure 5:
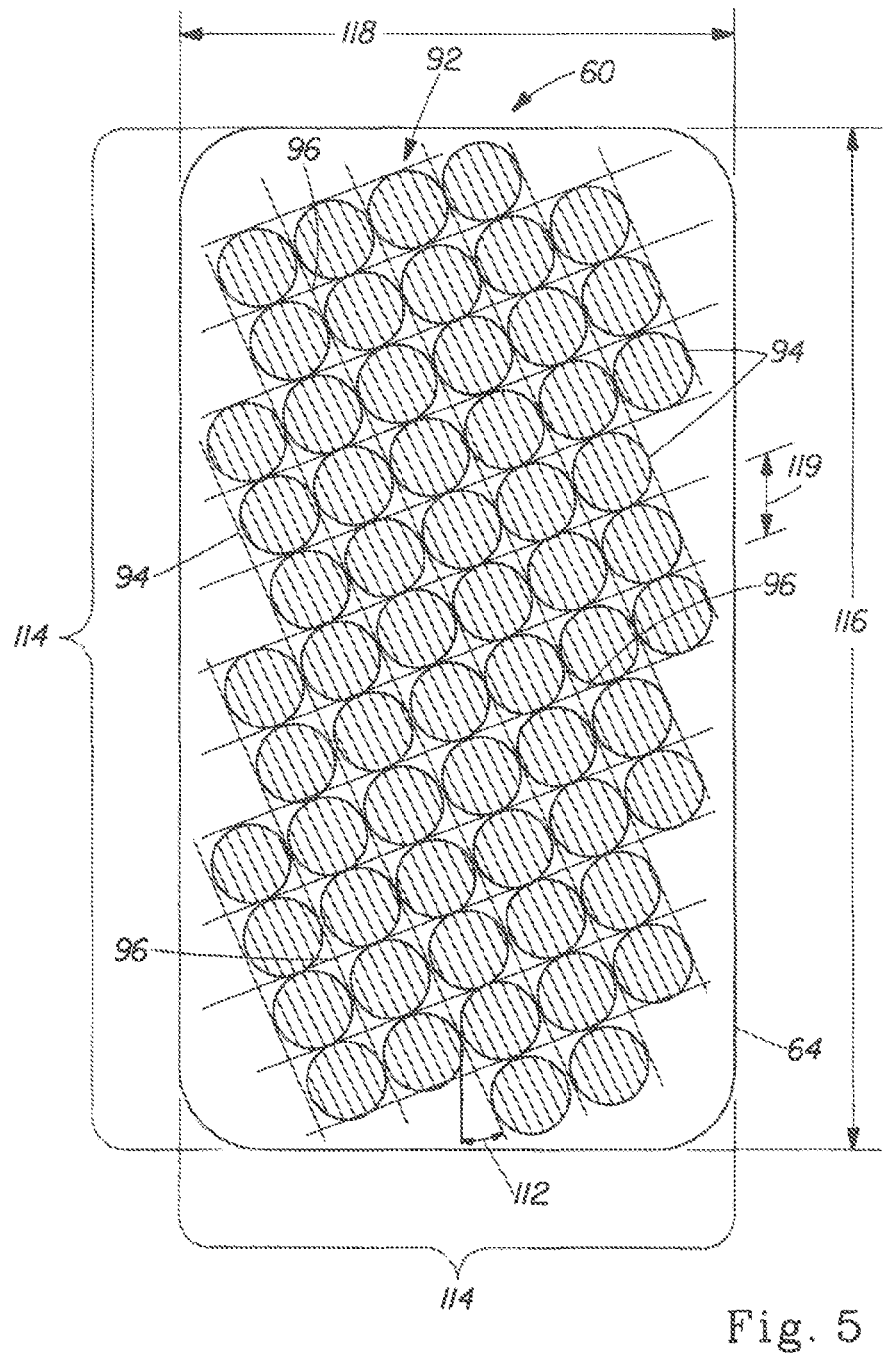
FIG. 5 is a plan view of the absorbent core layer illustrated in FIG. 3.
Figure 6:
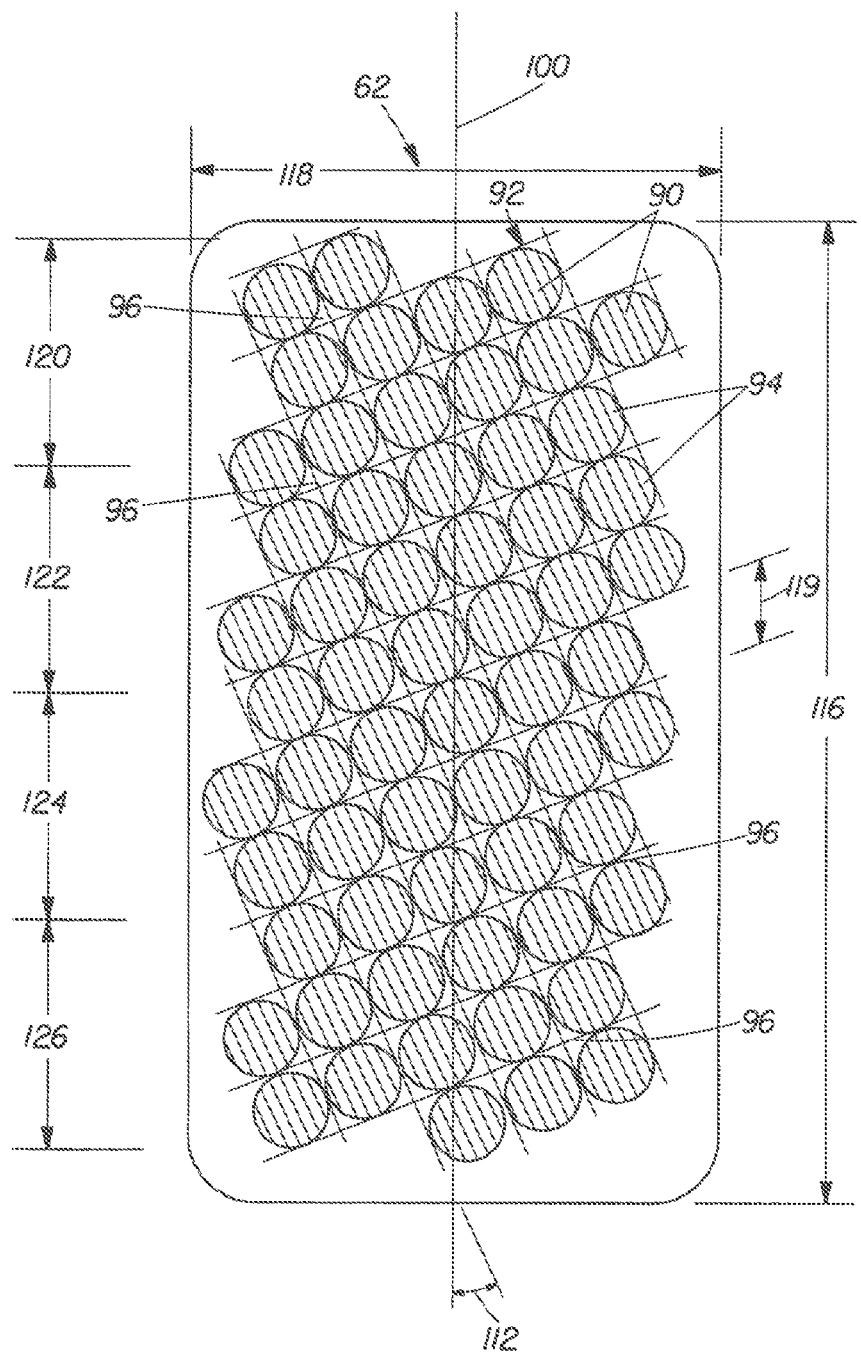
FIG. 6 is a plan view of a second absorbent core layer in accordance with an embodiment of this invention.

In operation, the printing system 130 receives the first and second substrate 64 and 72 into the first and second printing units 132 and 134, respectively, the first substrate 64 is drawn by the rotating first support roll 140 past the first auxiliary adhesive applicator 136 which applies the first auxiliary adhesive to the first substrate 64 in a pattern such as described hereinabove. A vacuum (not shown) within the first support roll 140 draws the first substrate 64 against the vertical support grid 166 and holds the first substrate 64 against the first support roll 140. This presents an uneven surface on the first substrate 64. Due to gravity, or by using the vacuum means, the substrate 64 will follow the contours of the uneven surface and thereby the substrate 64 will assume a mountain and valley shape. The absorbent particulate polymer material 66 may accumulate in the valleys presented by the substrate 64. The first support roll 140 then carries the first substrate 64 past the rotating first printing roll 144 which transfers the absorbent particulate polymer material 66 from the first hopper 142 to the first substrate 64 in the grid pattern 92 which is best illustrated in FIGS. 5 and 6. A vacuum (not shown) in the first printing roll 144 may hold the absorbent particulate polymer material 66 in the reservoirs 170 until time to deliver the absorbent particulate polymer material 66 to the first substrate 64. The vacuum may then be released or air flow through the air passages 174 may be reversed to eject the absorbent particulate polymer material 66 from the reservoirs and onto the first substrate 64. The absorbent particulate polymer material 66 may accumulate in the valleys presented by the substrate 64. The support roll 140 then carries the printed first substrate 64 past the thermoplastic adhesive material applicator 136 which applies the thermoplastic adhesive material 68 to cover the absorbent particulate polymer material 66 on the first substrate 64.

Hence, the uneven surface of the vented support grid 166 of the support rolls 140 and 152 determines the distribution of absorbent particulate polymeric material 66 and 74 throughout the absorbent core 14 and likewise determines the pattern of junction areas 96.

Meanwhile, the second rotatable support roll draws the second substrate 72 past the second auxiliary adhesive applicator 148 which applies an auxiliary adhesive to the second substrate 72 in a pattern such as is described hereinabove. The second rotatable support roll 152 then carries the second substrate 72 past the second printing roll 156 which transfers the absorbent particulate polymer material 74 from the second hopper 154 to the second substrate 72 and deposits the absorbent particulate polymer material 74 in the grid pattern 92 on the second substrate 72 in the same manner as described with regard to the first printing unit 132 above. The second thermoplastic adhesive material applicator 158 then applies the thermoplastic adhesive material 76 to cover the absorbent particulate polymer material 74 on the second substrate 72. The printed first and second substrates 64 and 72 then pass through the nip 162 between the first and second support rolls 140 and 152 for compressing the first absorbent layer 60 and second absorbent layer 62 together to form the absorbent core 14.

In an optional further process step a cover layer 70 may be placed upon the substrates 64 and 72, the absorbent particulate polymer material 66 and 74, and the thermoplastic adhesive material 68 and 76. In another embodiment, the cover layer 70 and the respective substrate 64 and 72 may be provided from a unitary sheet of material. The placing of the cover layer 70 onto the respective substrate 64 and 72 may then involve the folding of the unitary piece of material.

The test method and apparatuses described below may be useful in testing embodiments of this invention:

Wet Immobilization Test

Equipment
- Graduated Cylinder
- Stop watch (±0.1 sec)
- Scissors
- Light Box
- Pen
- Test solution: 0.90% saline solution at 37° C.
- Metal ruler traceable to NIST, DIN, JIS or other comparable National Standard
- PVC/metal dishes with a flat surface inside and a minimum length of the core bag length (n) to be measured and a maximum length n+30 mm, width of 105±5 mm, height of 30 –80 mm or equivalent
- Electronic Force Gauge (Range 0 to 50 Kg)
- Wet Immobilization Impact Tester Equipment (WAIIT), Design package number: BM-00112.59500-R01 available from T.M.G. Technisches Buero Manfred Gruna Facilities:
Standard laboratory conditions, temperature: 23° C.±2° C., relative humidity: <55%

Sample Preparation
1. Open the product, topsheet side up.
2. Unfold the diaper and cut the cuff elastics approximately every 2.5 cm to avoid chassis tension.
3. For pull-up products open the side seams and remove the waistbands.
4. Lay the core bag flat and rectangular topsheet side up onto the light box surface without any folds.
5. Switch on the light box to clearly identify the absorbent core outer edges.
6. With a ruler, draw a line at the front and back absorbent core outer edges.
7. Measure the distance (A), between the two markers and divide the value by 2, this will be calculated distance (B).
8. Measure the calculated distance (B) from front marker towards the middle of the core bag and mark it. At this marker draw a line in the cross direction.

Test Procedure

WAIIT Calibration:
1. Make sure that the sliding board is in the lower position. Open the front door of the WAIIT tester and connect the force gauge hook to the upper sample clamp of the WAIIT. Make sure that the clamp is closed before connecting the spring-balance.
2. Use both hands on the spring-balance to lift continuously and as slowly as possible up the sliding board towards the upper position. Record the average value ($m_1$) during the execution to the nearest 0.02 kg.
3. Guide down the sliding board as slowly as possible to the lower position and record the average value ($m_2$) read off during execution to the nearest 0.02 kg.

4. Calculate and report the delta of $m_1-m_2$ to the nearest 0.01 kg. If the delta is 0.6 kg±0.3 kg continue measurement. Otherwise, an adjustment of the sliding board is necessary. Make sure that the sliding board is in lower position and check the sliding path for any contamination or damage. Check if the position of the sliding board to the sliding path is correctly adjusted by shaking the board. For easy gliding some clearance is needed. If not present, readjust the system.

WAIIT Test Settings:
Drop height is 50 cm.
Diaper load ($I_D$) is 73% of the core capacity (cc); $I_D$=0.73×cc.
Core capacity (cc) is calculated as: cc=$m_{SAP}$×$SAP_{GV}$, where $m_{SAP}$ is the mass of superabsorbent polymer (SAP) present in the diaper and $SAP_{GV}$ is the free swelling capacity of the superabsorbent polymer. Free swelling capacity of the superabsorbent polymer is determined with the method described in WO 2006/062258. The mass of the superabsorbent polymer present in the diaper is the average mass present in ten products.

Test execution:
1. Reset the balance to zero (tare), put the dry core bag on the balance, weigh and report it to the nearest 0.1 g.
2. Measure the appropriate volume Saline (0.9% NaCl in deionized water) with the graduated cylinder.
3. Lay the core bag, topsheet side up, flat into the PVC dish. Pour the saline evenly over the core bag.
4. Take the PVC dish and hold it slanting in different directions, to allow any free liquid to be absorbed. Products with poly-backsheet need to be turned after a minimum waiting time of 2 minutes so that liquid under the backsheet can be absorbed. Wait for 10 minutes (+/−1 minute) to allow all saline to be absorbed. Some drops may retain in the PVC dish. Use only the defined PVC/metal dish to guarantee homogenous liquid distribution and less retained liquid.
5. Reset the balance to zero (tare), put the wet core bag on the balance. Weigh and report it to the nearest 0.1 g. Fold the core bag just once to make it fit on the balance. Check to see if the wet core bag weight is out of limit (defined as "dry core bag weight+diaper load±4 ml"). For example, 12 g dry core bag weight+150 ml load=162 g wet core bag weight. If the actual wet weight on the scale is between 158 g and 166 g, the pad can be used for shaking. Otherwise scrap the pad and use the next one.
6. Take the loaded core bag and cut the pad along the marked line in the cross direction.
7. Put the back of the wet core bag onto the balance (ml). Weigh and report it to the nearest 0.1 g.
8. Take the wet core and clamp the end seal side in the top clamp of the sample holder of the WAIIT (open end of the core oriented down). Next, clamp both sides of the core with the side clamps of the sample holder making sure that the product is fixed to the sample holder along the whole product length. Make sure not to clamp the absorbent core, only the nonwoven; for some products this means securing the product with only the barrier leg cuff.
9. Lift up the sliding board to the upper position by using both hands until the board is engaged.
10. Close the safety front door and release the slide blade.
11. Reset the balance to zero (tare), take the tested core bag out of the WAIIT and put it on the balance ($m_2$). Report the weight to the nearest 0.1 g.
12. Repeat steps 7 to 11 with front of the wet core bag.

Reporting:
1. Record the dry core bag weight to the nearest 0.1 g.
2. Record the wet weight before ($m_{1\ front/back}$) and after ($m_{2\ front/back}$) testing, both to the nearest 0.1 g.
3. Calculate and report the average weight loss (Δm) to the nearest 0.1 g: $\Delta m=(m_{1\ front}+m_{1\ back})-(m_{2\ front}+m_{2back})$
4. Calculate and report the weight loss in percent to the nearest 1%, ($\Delta m_{rel}$): $\Delta m_{rel}=(((m_{1front}+m_{1back})-(m_{2front}+m_{2back}))\times 100)/(m_{1front}+m_{1back})$
5. Calculate and report Wet Immobilization (WI) as: WI=100%−$\Delta m_{rel}$ All patents and patent applications (including any patents which issue thereon) assigned to the Procter & Gamble Company referred to herein are hereby incorporated by reference to the extent that it is consistent herewith.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising:
  a chassis including a topsheet and a backsheet; and
  a substantially cellulose free absorbent core located between the topsheet and the backsheet and including first and second absorbent layers, the first absorbent layer including a first substrate and the second absorbent layer including a second substrate, the first and second absorbent layers further including absorbent particulate polymer material deposited on said first and second substrates and thermoplastic adhesive material covering the absorbent particulate polymer material on the respective first and second substrates, said first and second absorbent layers combined together such that at least a portion of said thermoplastic adhesive material of said first absorbent layer contacts at least a portion of the thermoplastic adhesive material of said second absorbent layer, the absorbent particulate polymer material is disposed between the first and second substrates in an absorbent particulate polymer material area, and the absorbent particulate polymer material is substantially continuously distributed across the absorbent particulate polymer material area;
  wherein the absorbent particulate polymer material is deposited on the first and second substrates in respective patterns of land areas and junction areas between the land areas such that the absorbent particulate polymer material is discontinuously distributed on the first and second substrates; and the first and second absorbent layers are combined together such that the respective patterns of absorbent particulate polymer material are offset from one another;

wherein the absorbent core has a front end and a rear end and a longitudinal axis extending from the rear end to the front end and the land areas of the respective patterns are arranged in a grid which is positioned at an angle from about 5 to about 85 degrees from the longitudinal axis of the absorbent core;

wherein the width of the land areas is from about 8mm to about 12mm and the width of the junction areas is less than about 5mm;

wherein the absorbent core has four absorbent zones disposed along said longitudinal axis of said absorbent core, each of the four absorbent zones having absorbent particulate polymer material present in differing amounts between the four absorbent zones and each of the four absorbent zones is substantially cellulose free;

wherein there is a gradual transition in amount of absorbent particulate polymer material from one of the four absorbent zones to another.

2. The disposable absorbent article of claim 1, wherein the absorbent particulate polymer material area extends substantially entirely across the absorbent core.

3. The disposable absorbent article of claim 1, wherein the absorbent particulate polymer material area extends substantially entirely from front to back of the absorbent core.

4. The disposable absorbent article of claim 1, wherein the respective patterns are substantially the same.

5. The disposable absorbent article of claim 1, wherein the respective patterns are different.

6. The disposable absorbent article of claim 1, wherein the absorbent core consists essentially of the first and second substrates, the absorbent particulate polymer material, and the thermoplastic adhesive material.

7. The disposable absorbent article of claim 1, wherein the backsheet has a water vapor transmission rate of greater than about 3000 $g/24\ h/m^2$ according to the test described herein.

8. The disposable absorbent article of claim 1 having an absorbent particulate polymer material loss of no more than about 70% according to the Wet Immobilization Test herein.

9. The disposable absorbent article of claim 1, wherein the absorbent particulate polymer material is present in the absorbent core in an amount greater than about 80% by weight of the absorbent core.

10. The disposable absorbent article of claim 1, wherein the absorbent core has a length extending from a rear end to a front end, and a width extending from a first edge to a second edge and perpendicularly to the length, and the respective patterns are offset from one another in both a direction parallel to the length and d direction parallel to the width.

11. The disposable absorbent article of claim 1, wherein the absorbent article is a diaper comprising a re-closable fastening system joined to the chassis for securing the diaper to a wearer.

12. The disposable absorbent article of claim 1, wherein the absorbent article is a pant-type diaper comprising at least two side panels joined to the chassis and to each other to form a pant.

13. An absorbent core comprising first and second absorbent layers, the first absorbent layer including a first substrate and the second absorbent layer including a second substrate, the first and second absorbent layers further including absorbent particulate polymer material deposited on said first and second substrates and thermoplastic adhesive material covering the absorbent particulate polymer material on the respective first and second substrates, said first and second absorbent layers combined together such that at least a portion of said thermoplastic adhesive material of said first absorbent layer contacts at least a portion of the thermoplastic adhesive material of said second absorbent layer, the absorbent particulate polymer material is disposed between the first and second substrates in an absorbent particulate polymer material area, and the absorbent particulate polymer material is substantially continuously distributed across the absorbent particulate polymer material area, wherein the absorbent core is substantially cellulose free;

wherein the absorbent particulate polymer material is deposited on the first and second substrates in respective patterns of land areas and junction areas between the land areas such that the absorbent particulate polymer material is discontinuously distributed on the first and second substrates; and the first and second absorbent layers are combined together such that the respective patterns of absorbent particulate polymer material are offset from one another;

wherein the absorbent core has a front end and a rear end and a longitudinal axis extending from the rear end to the front end and the land areas of the respective patterns are arranged in a grid which is positioned at an angle from about 5 to about 85 degrees from the longitudinal axis of the absorbent core;

wherein the width of the land areas is from about 8mm to about 12mm and the width of the junction areas is less than about 5mm;

wherein the absorbent core has four absorbent zones disposed along said longitudinal axis of said absorbent core, each of the four absorbent zones having absorbent particulate polymer material present in differing amounts between the four absorbent zones and each of the four absorbent zones is substantially cellulose free;

wherein there is a gradual transition in amount of absorbent particulate polymer material from one of the four absorbent zones to another.

\* \* \* \* \*